(12) United States Patent
Adamczyk et al.

(10) Patent No.: US 8,835,120 B2
(45) Date of Patent: Sep. 16, 2014

(54) ASSAY FOR CARDIAC TROPONIN-T (CTNT)

(75) Inventors: Maciej Adamczyk, Gurnee, IL (US); Jeffrey R. Brashear, Mundelein, IL (US); Phillip G. Mattingly, Third Lake, IL (US)

(73) Assignee: Abbott Laboratories, Abbott Park, IL (US)

(*) Notice: Subject to any disclaimer, the term of this patent is extended or adjusted under 35 U.S.C. 154(b) by 271 days.

(21) Appl. No.: 12/629,736

(22) Filed: Dec. 2, 2009

(65) Prior Publication Data

US 2011/0129818 A1 Jun. 2, 2011

(51) Int. Cl.
*G01N 33/53* (2006.01)
(52) U.S. Cl.
USPC ............................................ 435/7.1; 435/7.2
(58) Field of Classification Search
None
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio | |
| 4,366,241 A | 12/1982 | Tom et al. | |
| 5,006,309 A | 4/1991 | Khalil et al. | |
| 5,011,771 A * | 4/1991 | Bellet et al. | 435/7.94 |
| 5,063,081 A | 11/1991 | Cozzette et al. | |
| 5,089,424 A | 2/1992 | Khalil et al. | |
| 5,241,070 A | 8/1993 | Law | |
| 5,244,630 A | 9/1993 | Khalil et al. | |
| 5,434,087 A * | 7/1995 | Beggs et al. | 436/505 |
| 5,468,646 A | 11/1995 | Mattingly et al. | |
| 5,543,524 A | 8/1996 | Mattingly et al. | |
| 5,783,699 A | 7/1998 | Mattingly et al. | |
| 6,268,481 B1 | 7/2001 | Morjana | |
| 6,376,206 B1 | 4/2002 | Katus et al. | |
| 6,670,115 B1 | 12/2003 | Zhang | |
| 6,682,648 B1 | 1/2004 | MacPhee et al. | |
| 6,887,714 B2 | 5/2005 | Fritsch et al. | |
| 7,045,310 B2 | 5/2006 | Buck, Jr. et al. | |
| 7,045,364 B2 | 5/2006 | Limoges et al. | |
| 7,371,582 B2 | 5/2008 | Nahm et al. | |
| 7,501,287 B2 * | 3/2009 | Orning | 436/505 |
| 7,776,605 B2 | 8/2010 | Mattingly et al. | |
| 2003/0170881 A1 | 9/2003 | Davis et al. | |
| 2004/0018577 A1 | 1/2004 | Emerson Campbell et al. | |
| 2005/0054078 A1 | 3/2005 | Miller et al. | |
| 2006/0160164 A1 * | 7/2006 | Miller et al. | 435/7.93 |
| 2008/0032929 A1 | 2/2008 | Jin | |
| 2009/0162876 A1 | 6/2009 | Adamczyk et al. | |
| 2010/0311079 A1 * | 12/2010 | Mattingly et al. | 435/7.1 |
| 2011/0085976 A1 | 4/2011 | Yan et al. | |

FOREIGN PATENT DOCUMENTS

| | | |
|---|---|---|
| CN | 2783324 Y | 5/2006 |
| EP | 425633 B1 | 7/1994 |
| EP | 273115 B1 | 9/1994 |
| EP | 424634 B1 | 6/1995 |
| EP | 406473 B1 | 9/1995 |
| EP | 326100 B1 | 9/1996 |
| EP | 1890154 A1 | 2/2008 |
| WO | 2007138163 A2 | 12/2007 |

OTHER PUBLICATIONS

O'Brien et al. (Laboratory Animals 2006 vol. 40, p. 153-171).*
Scott et al. (Nephrol Dial Transplant 2003 vol. 18, p. 737-742).*
Sodi et al. Clinical Chem. 2004 vol. 50, p. 786-787.*
Adamczyk et al., "Linker-Mediacted Modulation of the Cheiluminescent Signal From N10-(3-Sulfopropyl)-N-Sulfonylacridinium-9-carboxamide Tracers," Bioconjugate Chem, 2000, pp. 714-724, vol. 11.
Adamczyk et al., "Modulation of the Chemiluminescent Signal From N10-(3-Sulfopropyl)-N-Sulfonylacridinium-9-carboxamides," Tetrahedron, 1999, pp. 10899-10914, vol. 55.
Adamczyk et al., "Neopentyl 3-Triflyloxypropanesulfaonate Areactive Sulfopropylation Reagent for the Preparation of Chemiluminescent Labels," J Org Chem, 1998, pp. 5636-5639, vol. 63.
Adamczyk et al., "Regiodependent Luminescence Quenching of Biotinylated N-Sulfonyl-acridinium-9-carboxamides by Avidin," Organic Letters, 2003, pp. 3779-3782, vol. 5 (21).
Adamczyk et al., "Synthesis of a Chemiluminescent Acridinium Hydroxylamine (AHA) for the Direct Detection of Abasic Sites in DNA," Organic Letters, 1999, pp. 779-781, vol. 1 (5).
Akerstrom et al., "Protein G: A Powerful Tool for Binding and Detection of Monoclonal and Polyclonal Antibodies'," Immunology, 1985, vol. 135 (4) pp. 2589-2592.
Amgad N. Makaryus, et al, "Prevalence of Autoantibodies to Cardiac Troponin T Healthy Blood Donors" Clinical Chemistry, vol. 55 (8), 1592, 2009.
Clackson T., et al., "Making antibody fragments using phage display libraries," Nature,, 1991, 352, 624-628.
Cobbaert C., et al, "Do NIST SRM 2921 and recombinant cTnI-based serum pools have potential to harmonize cTnI results?" Ned Tijdschr Klin Chem Labgeneesk , 32, 175-178, 2007.
Coligan, et al., Current Protocols in Protein Science, TOC, U.S. Appl. No. 12/443,492, filled Oct. 12, 2007.
Co-pending U.S. Appl. No. 06/921,979.
Co-pending U.S. Appl. No. 07/150,278.
Co-pending U.S. Appl. No. 07/375,029.

(Continued)

*Primary Examiner* — Jacob Cheu
(74) *Attorney, Agent, or Firm* — Irene M. Reininger

(57) ABSTRACT

The present disclosure describes immunoassays for detecting cardiac troponin-T (cTnT) in a test sample, and in particular immunoassays and kits for detecting cTnT in a test sample suspected of containing substances that may interfere with the determination of cTnT, such as heterophilic endogenous antibodies and autoantibodies to cTnT. The methods use more than one capture phase antibody and more than one detection antibody to improve specificity, and provide for the use of humanized immunoreagents to overcome heterophilic antibody interferences.

11 Claims, 5 Drawing Sheets

(56) References Cited

OTHER PUBLICATIONS

Daniel P. Stites, et al, "Basic and Clinical Immunology" Lange medical book, 1991.
David J. Asai, et al, "Methods in Cell Biology" Antibodies in Cell Biology, vol. 37, 1993.
Goran Kronvall, et al, "A Surface Component in Group A, C, and G Streptococci With Non-Immune Reactivity for Immunoglobulin G" Boilinology, vol. 111 (5), 1973.
Griffiths A. D., et al., "Human anti-self antibodies with high specificity from phage display libraries," The EMBO J, 1993, 12 (2), 725-734.
Hoogenboom H. R., et al., Multi-subunit proteins on the surface of filamentous phage: methodologies for displaying antibody (Fab) heavy and light chains, Nucleic Acids Research, 1991, 19 (15), Oxford University Press, 4133-4137.
Kohler G., et al., "Continuous cultures of fused cells secreting antibody of predefined specificity," Nature , 1975, 256 (5517), 495-497.
Langone, et al, "Production of Antisera with Small Doses of Immunogen: Multiple Intradermal Injections", MethodsEnzymology, vol. 73, 46-52, 1981.
Mahalingam, et al, JAMA, vol. 278, 2143-2144, 1997.
Marks J. D. et al., "By-passing immunization. Human antibodies from V-gene libraries displayed on phage," J Mol Biol, 1991, vol. 222, pp. 581-597.
Marks, J.D. et al. (1992). "By-Passing Immunization: Building High Affinity Human Antibodies by Chain Shuffling," Bio/Technol. 10:779:783.
Mattingly et al., "Chemiluminescent N-Sulfonylacridinium-9-Carboxamides and Their Application in Clinical Assays," Luminescence Biotechnology: Instruments and Applications (CRC Press: Boca Raton 2000), 2002, pp. 77-105.
Mattingly Phillip G., "Chemiluminescent 10-Methyl-Acridinium-9(N-Sulphonylcarboxamide) Salts. Synthesis and Kinetics of Light Emission," Journal of Bioluminescence and Chemiluminescence, 1991, pp. 107-114, vol. 6.
McCafferty J., et al., "Phage antibodies: filamentous phage displaying antibody variable domains," Nature, 1990, 348, 552-554.
McCapra, et al., "Chemiluminescence Involving Peroxide Decompositions", Photochemistry and Photobiology, 1965, 4, 1111-1121.
Razavi, "Stable and versatile active acridinium esters I," Luminescence, 2000, pp. 239-244, vol. 15.
Razavi, "Stable and versatile active acridinium esters II," Luminescence, 2000, pp. 245-249, vol. 15.
Shayanfar, et al, "False-positive cardiac troponin T due to assay interference with heterophilic antibodies", 138, 31-32, 2008.
White et al., "Heterophilic Antibody Interference with Cardiac T Quantitative Rapid Assay", Clinical Chemistry, 48 (1), 201-202, 2002.
International Search Report and Written Opinion for Application No. PCT/US2010/057004, mailed on Feb. 7, 2011, 11 pages.
Murthy et al., Journal of Clinical Laboratory Analysis, "Troponin-T as a Serum Marker for Myocardial Infarction", 1997, vol. 11, pp. 125-128.
Co-pending U.S. Appl. No. 12/630,229, filed Dec. 3, 2009.
Henares T.G., et al., "Current Development in Microfluidic Immunosensing Chip," Analytica Chimica Acta, 2008, vol. 611 (1), pp. 17-30.
International Search Report and Written Opinion for Application No. PCT/US2010/056992, mailed on Jan. 31, 2011, 11 pages.
Kenny P.R., et al., "Falsely Elevated Cardiac Troponin-I in Patients with Seropositive Rheumatoid Arthritis," Journal of Rheumatology, 2005, vol. 32 (7), pp. 1258-1261.
Knoblcok R.J., et al., "False-Positive AxSYM Cardiac Troponin I Results in a 53-Year-Old Woman," Archives of Pathology & Laboratory Medicine, 2002, vol. 126 (5), pp. 606-609.
Makaryus A.N., et al., "Falsely Elevated Cardiac Troponin I Levels," Clinical Cardiology, 2007, vol. 30 (2), pp. 92-94.
Marquette C.A., et al., "Disposable Screen-Printed Chemiluminescent Biochips for the Simultaneous Determination of Four Point-of-Care Relevant Proteins," Analytical and Bioanalytical Chemistry, 2009, vol. 393 (4), pp. 1191-1198.
Co-pending U.S. Appl. No. 06/921,979, filed 1986.
Co-pending U.S. Appl. No. 07/150,278, filed 1988.
Co-pending U.S. Appl. No. 07/375,029, filed 1989.

\* cited by examiner

SDIEEVVEEY.EEEEQEEAAV EEEEDWREDE DEQEEAAEED AEAEAETEET
RAEEDEEEEE AKEAEDGPME ESKPKPRSFM PNLVPPKIPD GERVDFDDIH
RKRMEKDLNE LQALIEAHFE NRKKEEEELV SLKDRIERRR AERAEQQRIR
NEREKERQNR LAEERARREE EENRRKAEDE ARKKKALSNM MHFGGYIQKQ
AQTERKSGKR QTEREKKKKI LAERRKVLAI DHLNEDQLRE KAKELWQSIY
NLEAEKFDLQ EKFKQQKYEI NVLRNRINDN QKVSKTRGKA KVTGRWK (297 aa)

FIG. 2

ASSAY FOR CARDIAC TROPONIN-T (CTNT)

RELATED APPLICATION INFORMATION

None.

INCORPORATION OF SEQUENCE LISTING

The entire contents of a paper copy of the "Sequence Listing" and a computer readable form of the sequence listing on diskette, containing the file named 404360_Sequence_Listing_ST25.txt, which is 25 kilobytes in size and was created on Feb. 9, 2010, are herein incorporated by reference.

TECHNICAL FIELD

The present disclosure relates generally to assays and kits for detecting cardiac troponin-T (cTnT) in a test sample, and in particular to methods and kits for detecting cTnT in a test sample suspected of containing substances that may interfere with the determination of cTnT.

BACKGROUND OF THE INVENTION

Immunoassay techniques have been known for the last few decades and are now commonly used in medicine for a wide variety of diagnostic purposes to detect target analytes in a biological sample. Immunoassays exploit the highly specific binding of an antibody to its corresponding antigen, wherein the antigen is the target analyte. Typically, quantification of either the antibody or antigen is achieved through some form of labeling such as radio- or fluorescence-labeling. Sandwich immunoassays involve binding the target analyte in the sample to the antibody site (which is frequently bound to a solid support), binding labeled antibody to the captured analyte, and then measuring the amount of bound labeled antibody, wherein the label generates a signal proportional to the concentration of the target analyte inasmuch as labeled antibody does not bind unless the analyte is present in the sample.

Cardiac troponins are sensitive and specific biomarkers of cardiac injury. In particular, cTnT is highly cardiac specific, and it is not present in serum following non-myocardial muscle or other tissue damage. In addition, cTnT has been shown to be a more persistent and sensitive biomarker than others used for diagnosing myocardial infarction. Thus cardiac troponins generally are generally useful for diagnosing acute myocardial ischemia, and cTnT is especially useful. Currently a single assay is available for cTnT detection, from Roche Diagnostics. The assay is reportedly limited to detecting human cTnT from human heart tissue to only 7%. (C. Cobbaert et al, Mv. Ned Tijdschr KIM Chem Labgeneesk 2007; 32:175-8). Additionally, like many others, assays for cTnT are subject to interference heterophilic endogenous antibodies, which produce false positive results and thus misdiagnosis (G. H. White et al., Clin Chem 2002; 48:201-3; N. Shayanfar et al., Swiss Med Wkly 2008; 138:470). False negatives have also been reported. (See, e.g., Mahalingam M, Ottlinger M E. False-negative qualitative cardiac troponin in a 79-year-old man with myocardial infarction. JAMA 1997; 278:2143-4.J).

Additionally, the known assay for cTnT fails to address the problem of circulating endogenous antibodies, or "autoantibodies". Autoantibodies have been described for cTnT in apparently healthy blood donors (Adamczyk, M., Brashear, R. J., and Mattingly, P. G. (2009) Clin Chem 55, 1592-3; see also US Patent Application No. US20080102481A1). Other previously described autoantibodies are known to create interference in typical sandwich immunoassays composed of two or more analyte-specific antibodies. For example, cardiac troponin-I reactive autoantibodies may interfere with the measurement of cTnI using conventional midfragment-specific immunoassays. Thus, interference from autoantibodies can also produce erroneous results, particularly near the cut-off values established for clinical diagnoses, thereby increasing the risk of false negative diagnostic results and the risk that individuals will not obtain a timely diagnosis. Additionally, autoantibodies may react with antigens, forming macro-complexes which may extend the circulating half-life of the antigen beyond the typical course of the acute release of the antigen. One approach to addressing the problem of interference from autoantibodies is to choose analyte-specific antibodies that bind to specific epitopes distinct from the analyte epitopes that react with the autoantibodies. Following this general approach, efforts have focused on exploring the use of thousands of different combinations of two, three and even four analyte-specific antibodies to avoid interference from autoantibodies. However, this effort has been largely unsuccessful. It is now evident that autoantibodies against complex protein analytes are likely to be polyclonal within a particular sample, and may be even more diverse among samples from different individuals. Interference from diverse polyclonal autoantibodies may explain the observation that as little as 25% or even less of an analyte protein sequence binds to analyte-specific antibodies, which may in turn explain the lack of success using this approach.

A need therefore exists in the art for improved cTnT immunoassay methods that compensate for interference from various substances that may also be present in a test sample, and in particular for such methods that do so without involving redesign of the analyte detection or capture antibodies.

SUMMARY OF THE INVENTION

In one aspect, the present disclosure provides an immunoassay for quantifying an amount of cardiac troponin-T (cTnT) in a test sample, the immunoassay comprising the steps of:

a) contacting a test sample suspected of containing cTnT with n capture antibodies (C) that bind to at least n epitopes on cTnT to form a n-capture antibody: cTnT complex $(C_1)$ $(C_2)\ldots(Cn)(cTnT)$, wherein n is an integer from 1 to 10; and b) contacting said mixture comprising a n-capture antibody-cTnT epitope complex $(C_1)(C_2)\ldots(Cn)(cTnT)$ with n' detection antibodies (D) that bind to n' epitopes on cTnT to form a n'-detection antibody: n-capture antibody: cTnT measurable assembly $(D_1)(D_2)\ldots(Dn')(C_1)(C_2)\ldots(Cn)(cTnT)$, wherein n' and n are independently an integer from 1 to 10, and antibodies C and D bind to (n+n') different epitopes of cTnT.

In the immunoassay, an optical, electrical, or change-of-state signal of the measurable assembly can be measured. An optical signal may be measured as a cTnT concentration dependent change in chemiluminescence, fluorescence, phosphorescence, electrochemiluminescence, ultraviolet absorption, visible absorption, infrared absorption, refraction, surface plasmon resonance. An electrical signal may be measured as a cTnT dependent change in current, resistance, potential, mass to charge ratio, or ion count. Alternatively, the change-of-state signal may be measured as a cTnT concentration dependent change in size, solubility, mass, or resonance.

In the above immunoassay, the capture antibodies, the detection antibodies, or the capture and detection antibodies may comprise humanized antibodies.

In the above immunoassay, the detection antibodies can be conjugated to a detectable label, wherein the detectable label is an enzyme, oligonucleotide, nanoparticle chemiluminophore, fluorophore, fluorescence quencher, chemiluminescence quencher, or biotin.

In the above immunoassay, detection antibodies may comprise humanized antibodies complexed with an anti-human IgG antibody, which may be conjugated to a detectable label. The detectable label is for example an enzyme, oligonucleotide, nanoparticle chemiluminophore, fluorophore, fluorescence quencher, chemiluminescence quencher, or biotin.

In the above immunoassay, the capture antibodies may be immobilized on a solid phase. The solid phase may be selected from the group consisting of a magnetic particle, bead, test tube, microtiter plate, cuvette, membrane, a scaffolding molecule, quartz crystal, film, filter paper, disc and chip.

In another aspect, the present disclosure provides an immunoassay for quantifying an amount of cTnT in a test sample, the immunoassay comprising the steps of:

a) contacting a test sample suspected of containing cTnT with n capture antibodies (C) that bind to at least n epitopes on cTnT to form a n-capture antibody:cTnT complex $(C_1)(C_2)\ldots(Cn)(cTnT)$, wherein n is an integer from 1 to 10;

b) contacting said mixture comprising a n-capture antibody-cTnT epitope complex $(C_1)(C_2)\ldots(Cn)(cTnT)$ with n' detection antibodies (D) that bind to n' epitopes on cTnT to form a n'-detection antibody:n-capture antibody:cTnT measurable assembly $(D_1)(D_2)\ldots(Dn')(C_1)(C_2)\ldots(Cn)(cTnT)$, wherein the detection antibodies D are labeled with a detectable label comprising at least one acridinium compound, n' and n are independently an integer from 1 to 10, and antibodies C and D bind to (n+n') different epitopes of cTnT;

c) generating or providing a source of hydrogen peroxide to the mixture of step (b);

d) adding a basic solution to the mixture of step (c) to generate a light signal;

e) measuring the light signal generated by or emitted in step (d); and f) quantifying the amount of troponin-T in the test sample based on the measurement in step (e).

In the above immunoassay, the capture antibodies, the detection antibodies, or the capture and detection antibodies may comprise humanized antibodies.

In the above immunoassay, the detection antibodies may comprise humanized antibodies complexed with an anti-human IgG antibody conjugated to the detectable label that comprises at least one acridinium compound.

In the above immunoassay, any acridinium compound can be used. For example, the acridinium compound can be an acridinium-9-carboxamide having a structure according to formula I:

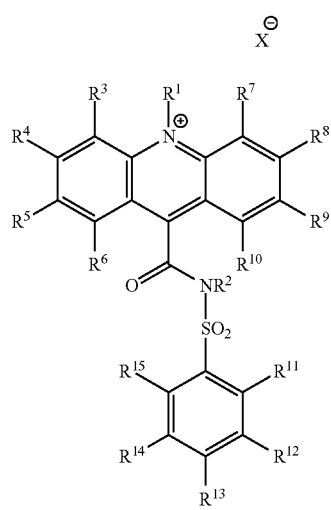

I wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^{\ominus}$ is an anion.

Alternatively, the acridinium compound is an acridinium-9-carboxylate aryl ester having a structure according to formula II:

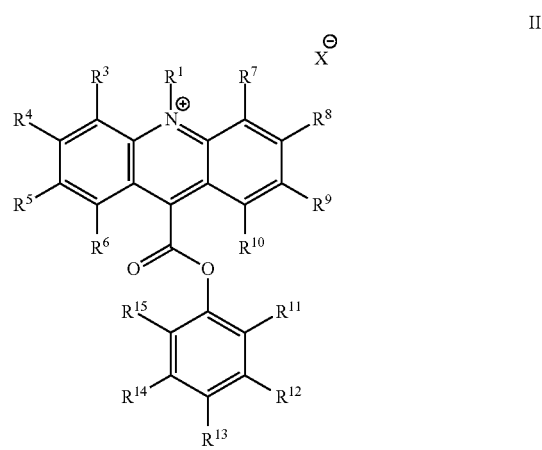

II wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^{\ominus}$ is an anion.

In the above immunoassay, the capture antibodies C may be immobilized on a solid phase. The solid phase may be selected from the group consisting of a magnetic particle, bead, test tube, microtiter plate, cuvette, membrane, a scaffolding molecule, quartz crystal, film, filter paper, disc and chip.

In the above immunoassay, the capture antibodies can be selected from the group consisting of a polyclonal antibody, a monoclonal antibody, a chimeric antibody, a human antibody, and an affinity maturated antibody. Additionally, the detection antibodies can be selected from the group consisting of a polyclonal antibody, a monoclonal antibody, a chimeric antibody, a human antibody, and an affinity maturated antibody.

In the above immunoassay, the hydrogen peroxide can be provided by adding a buffer or a solution containing hydrogen peroxide. The hydrogen peroxide can be generated by adding a hydrogen peroxide generating enzyme to the test sample. The hydrogen peroxide generating enzyme can be selected from the group consisting of: (R)-6-hydroxynicotine oxidase, (S)-2-hydroxy acid oxidase, (S)-6-hydroxynicotine oxidase, 3-aci-nitropropanoate oxidase, 3-hydroxyanthranilate oxidase, 4-hydroxymandelate oxidase, 6-hydroxynicotinate dehydrogenase, abscisic-aldehyde oxidase, acyl-CoA oxidase, alcohol oxidase, aldehyde oxidase, amine oxidase, amine oxidase (copper-containing), amine oxidase (flavin-containing), aryl-alcohol oxidase, aryl-aldehyde oxidase, catechol oxidase, cholesterol oxidase, choline oxidase, columbamine oxidase, cyclohexylamine oxidase, cytochrome c oxidase, D-amino-acid oxidase, D-arabinono-1,4-lactone oxidase, D-arabinono-1,4-lactone oxidase, D-aspartate oxidase, D-glutamate oxidase, D-glutamate(D-aspartate) oxidase, dihydrobenzophenanthridine oxidase, dihydroorotate oxidase, dihydrouracil oxidase, dimethylglycine oxidase, D-mannitol oxidase, ecdysone oxidase, ethanolamine oxidase, galactose oxidase, glucose oxidase, glutathione oxidase, glycerol-3-phosphate oxidase, glycine oxidase, glyoxylate oxidase, hexose oxidase, hydroxyphytanate oxidase, indole-3-acetaldehyde oxidase, lactic acid oxidase, L-amino-acid oxidase, L-aspartate oxidase, L-galactonolactone oxidase, L-glutamate oxidase, L-gulonolactone oxidase, L-lysine 6-oxidase, L-lysine oxidase, long-chain-alcohol oxidase, L-pipecolate oxidase, L-sorbose oxidase, malate oxidase, methanethiol oxidase, monoamino acid oxidase, N6-methyl-lysine oxidase, N-acylhexosamine oxidase, NAD(P)H oxidase, nitroalkane oxidase, N-methyl-L-amino-acid oxidase, nucleoside oxidase, oxalate oxidase, polyamine oxidase, polyphenol oxidase, polyvinyl-alcohol oxidase, prenylcysteine oxidase, protein-lysine 6-oxidase, putrescine oxidase, pyranose oxidase, pyridoxal 5'-phosphate synthase, pyridoxine 4-oxidase, pyrroloquinoline-quinone synthase, pyruvate oxidase, pyruvate oxidase (CoA-acetylating), reticuline oxidase, retinal oxidase, rifamycin-B oxidase, sarcosine oxidase, secondary-alcohol oxidase, sulfite oxidase, superoxide dismutase, superoxide reductase, tetrahydroberberine oxidase, thiamine oxidase, tryptophan α,β-oxidase, urate oxidase (uricase, uric acid oxidase), vanillyl-alcohol oxidase, xanthine oxidase, xylitol oxidase and combinations thereof.

In the above immunoassay, the basic solution can be for example a solution having a pH of at least about 10.

The above immunoassay may further comprise the step of quantifying the amount of the cTnT in the test sample by relating the amount of light signal in step (e) to the amount of cTnT in the test sample either by use of a standard curve for cTnT or by comparison to a reference standard. The reference standard may comprise an anti-idiotypic antibody. The reference standard may comprise a derivatized cTnT, such as for example cTnT derivatized with a polyethylene glycol.

The above immunoassay may be adapted for use in an automated system or semi-automated system.

In any of the above immunoassays, the test sample may be whole blood, serum, or plasma.

In another aspect, the present disclosure provides a kit for quantifying the amount of cTnT in a test sample, the kit comprising:

a) n capture antibodies (C) that bind to at least n epitopes on cTnT to form a n-capture antibody: cTnT complex $(C_1)(C_2) \ldots (Cn)(cTnT)$, wherein n is an integer from 1 to 10;

b) n' detection antibodies (D) that bind to n' epitopes on cTnT to form a n'-detection antibody:n-capture antibody: cTnT measurable assembly $(D_1)(D_2) \ldots (Dn')(C_1)(C_2) \ldots (Cn)(cTnT)$, wherein n' and n are independently an integer from 1 to 10; and wherein antibodies C and D bind to (n+n') different epitopes of cTnT; and c) instructions for quantifying the amount of troponin-T in the test sample.

In the above kit, the capture antibodies, the detection antibodies, or the capture and detection antibodies may comprise humanized antibodies.

In the above kit, the detection antibodies may comprise humanized antibodies complexed to an antihuman IgG antibody. The antihuman IgG antibody may be conjugated to the detectable label.

In the above kit, the capture antibodies may be bound to a solid phase. The solid phase can be selected from the group consisting of a magnetic particle, a bead, a test tube, a microtiter plate, a cuvette, a membrane, a scaffolding molecule, a quartz crystal, a film, a filter paper, a disc and a chip.

The above kit may further comprise a detectable label conjugated to the detection antibodies. The detectable label may be an enzyme, oligonucleotide, nanoparticle chemiluminophore, fluorophore, fluorescence quencher, chemiluminescence quencher, or biotin.

In the above kit, an acridinium compound can be used as the detectable label. For example, the acridinium compound can be an acridinium-9-carboxamide having a structure according to formula I:

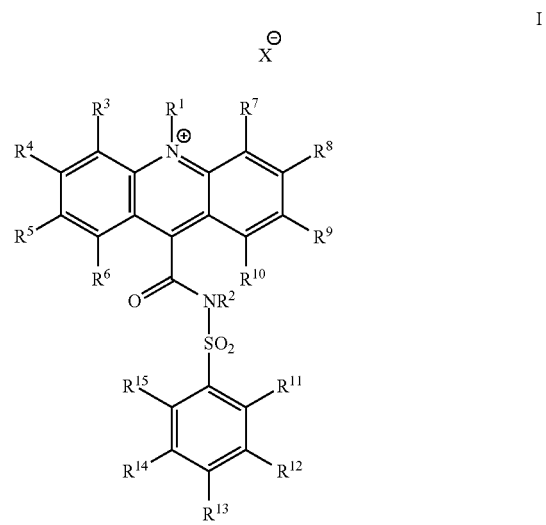

wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^{\ominus}$ is an anion.

Alternatively, in the above kit the acridinium compound is an acridinium-9-carboxylate aryl ester having a structure according to formula II:

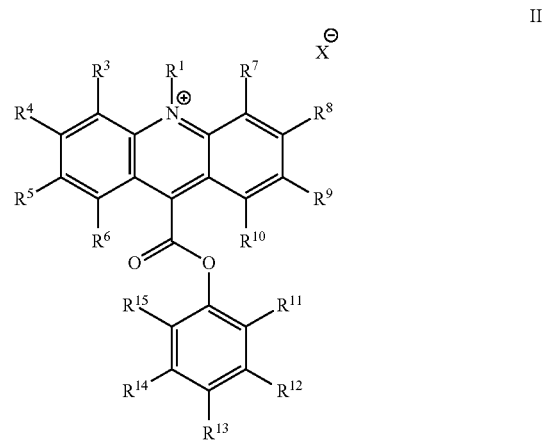

wherein R¹ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\ominus$ is an anion.

The above kit may further comprise a basic solution. The basic solution can be for example a solution having a pH of at least about 10.

The above kit may further include a hydrogen peroxide source, which can be a buffer, a solution containing hydrogen peroxide, or a hydrogen peroxide generating enzyme. In kits containing a hydrogen peroxide generating enzyme, the enzyme can be selected from the group consisting of: (R)-6-hydroxynicotine oxidase, (S)-2-hydroxy acid oxidase, (S)-6-hydroxynicotine oxidase, 3-aci-nitropropanoate oxidase, 3-hydroxyanthranilate oxidase, 4-hydroxymandelate oxidase, 6-hydroxynicotinate dehydrogenase, abscisic-aldehyde oxidase, acyl-CoA oxidase, alcohol oxidase, aldehyde oxidase, amine oxidase, amine oxidase (copper-containing), amine oxidase (flavin-containing), aryl-alcohol oxidase, aryl-aldehyde oxidase, catechol oxidase, cholesterol oxidase, choline oxidase, columbamine oxidase, cyclohexylamine oxidase, cytochrome c oxidase, D-amino-acid oxidase, D-arabinono-1,4-lactone oxidase, D-arabinono-1,4-lactone oxidase, D-aspartate oxidase, D-glutamate oxidase, D-glutamate(D-aspartate) oxidase, dihydrobenzophenanthridine oxidase, dihydroorotate oxidase, dihydrouracil oxidase, dimethylglycine oxidase, D-mannitol oxidase, ecdysone oxidase, ethanolamine oxidase, galactose oxidase, glucose oxidase, glutathione oxidase, glycerol-3-phosphate oxidase, glycine oxidase, glyoxylate oxidase, hexose oxidase, hydroxyphytanate oxidase, indole-3-acetaldehyde oxidase, lactic acid oxidase, L-amino-acid oxidase, L-aspartate oxidase, L-galactonolactone oxidase, L-glutamate oxidase, L-gulonolactone oxidase, L-lysine 6-oxidase, L-lysine oxidase, long-chain-alcohol oxidase, L-pipecolate oxidase, L-sorbose oxidase, malate oxidase, methanethiol oxidase, monoamino acid oxidase, N6-methyl-lysine oxidase, N-acyl-hexosamine oxidase, NAD(P)H oxidase, nitroalkane oxidase, N-methyl-L-amino-acid oxidase, nucleoside oxidase, oxalate oxidase, polyamine oxidase, polyphenol oxidase, polyvinyl-alcohol oxidase, prenylcysteine oxidase, protein-lysine 6-oxidase, putrescine oxidase, pyranose oxidase, pyridoxal 5'-phosphate synthase, pyridoxine 4-oxidase, pyrroloquinoline-quinone synthase, pyruvate oxidase, pyruvate oxidase (CoA-acetylating), reticuline oxidase, retinal oxidase, rifamycin-B oxidase, sarcosine oxidase, secondary-alcohol oxidase, sulfite oxidase, superoxide dismutase, superoxide reductase, tetrahydroberberine oxidase, thiamine oxidase, tryptophan α,β-oxidase, urate oxidase (uricase, uric acid oxidase), vanillyl-alcohol oxidase, xanthine oxidase, xylitol oxidase and combinations thereof.

The above kit may further comprise a cTnT reference standard. The cTnT reference standard may comprise, for example, an anti-idiotypic antibody. The cTnT reference standard may comprise a derivatized cTnT, such as for example cTnT derivatized with a polyethylene glycol.

BRIEF DESCRIPTION OF THE DRAWINGS

FIG. 2 is the amino acid sequence of Human cardiac troponin T (cTnT);

DETAILED DESCRIPTION

Figure 1:
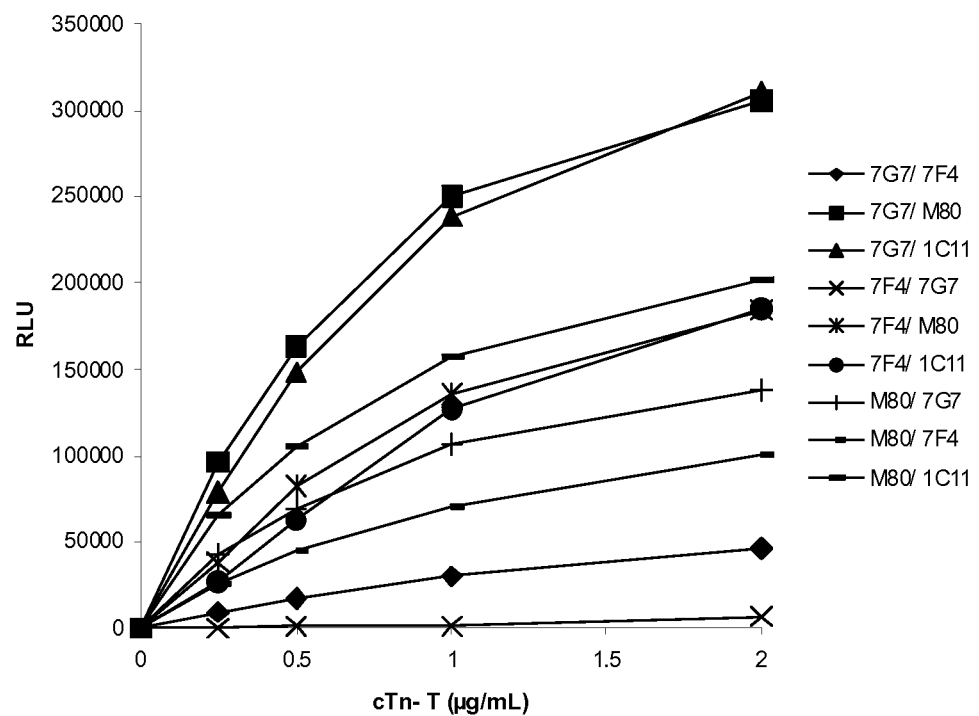
FIG. 1 is a graph of dose-response of different combinations of detection and capture antibodies.

The present disclosure provides an improved assay for quantifying an amount of cTnT in a test sample, and especially in a test sample suspected of containing substances that may interfere with the determination of cTnT in the sample. Such substances include but are not limited to, for example, endogenous anti-cTnT antibodies. The methods are based in part on the use of more than one capture phase antibody and more than one detection antibody to improve specificity. This assay approach compensates for the presence of other substances such as heterophilic endogenous antibodies, and autoantibodies that may be present in the test sample without redesign of the analyte-specific detection antibodies or the capture antibodies, and avoids the need of a second assay to identify problematic samples.

Additionally, the methods provide for the use of humanized immunoreagents to overcome heterophilic antibody interferences. Use of antihuman IgG detection antibody corrects for endogenous autoantibodies and when used in conjunction with humanized immunoreagents provides a "universal" signal generator. Derivatized cTnT provides a soluble reagent suitable for assay standardization.

A. DEFINITIONS

Section headings as used in this section and the entire disclosure herein are not intended to be limiting.

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

a) Acyl (and Other Chemical Structural Group Definitions)

As used herein, the term "acyl" refers to a —C(O)$R_a$ group where $R_a$ is hydrogen, alkyl, cycloalkyl, cycloalkylalkyl, phenyl or phenylalkyl. Representative examples of acyl include, but are not limited to, formyl, acetyl, cylcohexylcarbonyl, cyclohexylmethylcarbonyl, benzoyl, benzylcarbonyl and the like.

As used herein, the term "alkenyl" means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

As used herein, the term "alkyl" means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

As used herein, the term "alkyl radical" means any of a series of univalent groups of the general formula $C_nH_{2n+1}$ derived from straight or branched chain hydrocarbons.

As used herein, the term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

As used herein, the term "alkynyl" means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

As used herein, the term "amido" refers to an amino group attached to the parent molecular moiety through a carbonyl group (wherein the term "carbonyl group" refers to a —C(O)— group).

As used herein, the term "amino" means —$NR_bR_c$, wherein $R_b$ and $R_c$ are independently selected from the group consisting of hydrogen, alkyl and alkylcarbonyl.

As used herein, the term "aralkyl" means an aryl group appended to the parent molecular moiety through an alkyl group, as defined herein. Representative examples of aralkyl include, but are not limited to, benzyl, 2-phenylethyl, 3-phenylpropyl, and 2-naphth-2-ylethyl.

As used herein, the term "aryl" means a phenyl group, or a bicyclic or tricyclic fused ring system wherein one or more of the fused rings is a phenyl group. Bicyclic fused ring systems are exemplified by a phenyl group fused to a cycloalkenyl group, a cycloalkyl group, or another phenyl group. Tricyclic fused ring systems are exemplified by a bicyclic fused ring system fused to a cycloalkenyl group, a cycloalkyl group, as defined herein or another phenyl group. Representative examples of aryl include, but are not limited to, anthracenyl, azulenyl, fluorenyl, indanyl, indenyl, naphthyl, phenyl, and tetrahydronaphthyl. The aryl groups of the present disclosure can be optionally substituted with one-, two, three, four, or five substituents independently selected from the group consisting of alkoxy, alkyl, carboxyl, halo, and hydroxyl.

As used herein, the term "carboxy" or "carboxyl" refers to —$CO_2H$ or —$CO_2^-$.

As used herein, the term "carboxyalkyl" refers to a —$(CH_2)_nCO_2H$ or —$(CH_2)_nCO_2^-$ group where n is from 1 to 10.

As used herein, the term "cyano" means a —CN group.

As used herein, the term "cycloalkenyl" refers to a non-aromatic cyclic or bicyclic ring system having from three to ten carbon atoms and one to three rings, wherein each five-membered ring has one double bond, each six-membered ring has one or two double bonds, each seven- and eight-membered ring has one to three double bonds, and each nine-to ten-membered ring has one to four double bonds. Representative examples of cycloalkenyl groups include cyclohexenyl, octahydronaphthalenyl, norbornylenyl, and the like. The cycloalkenyl groups can be optionally substituted with one, two, three, four, or five substituents independently selected from the group consisting of alkoxy, alkyl, carboxyl, halo, and hydroxyl.

As used herein, the term "cycloalkyl" refers to a saturated monocyclic, bicyclic, or tricyclic hydrocarbon ring system having three to twelve carbon atoms. Representative examples of cycloalkyl groups include cyclopropyl, cyclopentyl, bicyclo[3.1.1]heptyl, adamantyl, and the like. The cycloalkyl groups of the present disclosure can be optionally substituted with one, two, three, four, or five substituents independently selected from the group consisting of alkoxy, alkyl, carboxyl, halo, and hydroxyl.

As used herein, the term "cycloalkylalkyl" means a —$R_dR_e$ group where $R_d$ is an alkylene group and $R_e$ is cycloalkyl group. A representative example of a cycloalkylalkyl group is cyclohexylmethyl and the like.

As used herein, the term "halogen" means a —Cl, —Br, —I or —F; the term "halide" means a binary compound, of which one part is a halogen atom and the other part is an element or radical that is less electronegative than the halogen, e.g., an alkyl radical.

As used herein, the term "hydroxyl" means an —OH group.

As used herein, the term "nitro" means a —$NO_2$ group.

As used herein, the term "oxoalkyl" refers to —$(CH_2)_nC(O)R_a$, where $R_a$ is hydrogen, alkyl, cycloalkyl, cycloalkylalkyl, phenyl or phenylalkyl and where n is from 1 to 10.

As used herein, the term "phenylalkyl" means an alkyl group which is substituted by a phenyl group.

As used herein, the term "sulfo" means a —$SO_3H$ group.

As used herein, the term "sulfoalkyl" refers to a —$(CH_2)$—$SO_3H$ or —$(CH_2)$—$SO_3^-$ group where n is from 1 to 10.

b) Anion

As used herein, the term "anion" refers to an anion of an inorganic or organic acid, such as, but not limited to, hydrochloric acid, hydrobromic acid, sulfuric acid, methane sulfonic acid, formic acid, acetic acid, oxalic acid, succinic acid, tartaric acid, mandelic acid, fumaric acid, lactic acid, citric acid, glutamic acid, aspartic acid, phosphate, trifluoromethansulfonic acid, trifluoroacetic acid and fluorosulfonic acid and any combinations thereof.

c) Antibody

As used herein, the term "antibody" refers to a protein consisting of one or more polypeptides substantially encoded by immunoglobulin genes or fragments of immunoglobulin genes, and encompasses polyclonal antibodies, monoclonal antibodies, and fragments thereof, as well as molecules engineered from immunoglobulin gene sequences. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

d) Hydrogen Peroxide Generating Enzyme

As used herein, the term "hydrogen peroxide generating enzyme" refers to an enzyme that is capable of producing as a reaction product the chemical compound having the molecular formula $H_2O_2$, i.e. hydrogen peroxide. Non-limiting examples of hydrogen peroxide generating enzymes are listed below in Table 1.

TABLE 1

| ACCEPTED COMMON NAME | IUBMB ENZYME NOMENCLATURE | PREFERRED SUBSTRATE |
|---|---|---|
| (R)-6-hydroxynicotine oxidase | EC 1.5.3.6 | (R)-6-hydroxynicotine |
| (S)-2-hydroxy acid oxidase | EC 1.1.3.15 | S)-2-hydroxy acid |
| (S)-6-hydroxynicotine oxidase | EC 1.5.3.5 | (S)-6-hydroxynicotine |
| 3-aci-nitropropanoate oxidase | EC 1.7.3.5 | 3-aci-nitropropanoate |

TABLE 1-continued

| ACCEPTED COMMON NAME | IUBMB ENZYME NOMENCLATURE | PREFERRED SUBSTRATE |
|---|---|---|
| 3-hydroxyanthranilate oxidase | EC 1.10.3.5 | 3-hydroxyanthranilate |
| 4-hydroxymandelate oxidase | EC 1.1.3.19 | (S)-2-hydroxy-2-(4-hydroxyphenyl)acetate |
| 6-hydroxynicotinate dehydrogenase | EC 1.17.3.3 | 6-hydroxynicotinate |
| Abscisic-aldehyde oxidase | EC 1.2.3.14 | abscisic aldehyde |
| acyl-CoA oxidase | EC 1.3.3.6 | acyl-CoA |
| Alcohol oxidase | EC 1.1.3.13 | a primary alcohol |
| Aldehyde oxidase | EC 1.2.3.1 | an aldehyde |
| amine oxidase | | |
| amine oxidase (copper-containing) | EC 1.4.3.6 | primary monoamines, diamines and histamine |
| amine oxidase (flavin-containing) | EC 1.4.3.4 | a primary amine |
| aryl-alcohol oxidase | EC 1.1.3.7 | an aromatic primary alcohol (2-naphthyl)methanol 3-methoxybenzyl alcohol |
| aryl-aldehyde oxidase | EC 1.2.3.9 | an aromatic aldehyde |
| Catechol oxidase | EC 1.1.3.14 | Catechol |
| cholesterol oxidase | EC 1.1.3.6 | Cholesterol |
| Choline oxidase | EC 1.1.3.17 | Choline |
| columbamine oxidase | EC 1.21.3.2 | Columbamine |
| cyclohexylamine oxidase | EC 1.4.3.12 | Cyclohexylamine |
| cytochrome c oxidase | EC 1.9.3.1 | |
| D-amino-acid oxidase | EC 1.4.3.3 | a D-amino acid |
| D-arabinono-1,4-lactone oxidase | EC 1.1.3.37 | D-arabinono-1,4-lactone |
| D-arabinono-1,4-lactone oxidase | EC 1.1.3.37 | D-arabinono-1,4-lactone |
| D-aspartate oxidase | EC 1.4.3.1 | D-aspartate |
| D-glutamate oxidase | EC 1.4.3.7 | D-glutamate |
| D-glutamate(D-aspartate) oxidase | EC 1.4.3.15 | D-glutamate |
| dihydrobenzophenanthridine oxidase | EC 1.5.3.12 | dihydrosanguinarine |
| dihydroorotate oxidase | EC 1.3.3.1 | (S)-dihydroorotate |
| dihydrouracil oxidase | EC 1.3.3.7 | 5,6-dihydrouracil |
| dimethylglycine oxidase | EC 1.5.3.10 | N,N-dimethylglycine |
| D-mannitol oxidase | EC 1.1.3.40 | Mannitol |
| Ecdysone oxidase | EC 1.1.3.16 | Ecdysone |
| ethanolamine oxidase | EC 1.4.3.8 | Ethanolamine |
| Galactose oxidase | EC 1.1.3.9 | D-galactose |
| Glucose oxidase | EC 1.1.3.4 | β-D-glucose |
| glutathione oxidase | EC 1.8.3.3 | Glutathione |
| Glycerol-3-phosphate oxidase | EC 1.1.3.21 | sn-glycerol 3-phosphate |
| Glycine oxidase | EC 1.4.3.19 | Glycine |
| glyoxylate oxidase | EC 1.2.3.5 | Glyoxylate |
| hexose oxidase | EC 1.1.3.5 | D-glucose, D-galactose D-mannose maltose lactose cellobiose |
| hydroxyphytanate oxidase | EC 1.1.3.27 | L-2-hydroxyphytanate |
| indole-3-acetaldehyde oxidase | EC 1.2.3.7 | (indol-3-yl)acetaldehyde |
| lactic acid oxidase | | Lactic acid |
| L-amino-acid oxidase | EC 1.4.3.2 | an L-amino acid |
| L-aspartate oxidase | EC 1.4.3.16 | L-aspartate |
| L-galactonolactone oxidase | EC 1.3.3.12 | L-galactono-1,4-lactone |
| L-glutamate oxidase | EC 1.4.3.11 | L-glutamate |
| L-gulonolactone oxidase | EC 1.1.3.8 | L-gulono-1,4-lactone |
| L-lysine 6-oxidase | EC 1.4.3.20 | L-lysine |
| L-lysine oxidase | EC 1.4.3.14 | L-lysine |
| long-chain-alcohol oxidase | EC 1.1.3.20 | A long-chain-alcohol |
| L-pipecolate oxidase | EC 1.5.3.7 | L-pipecolate |
| L-sorbose oxidase | EC 1.1.3.11 | L-sorbose |
| malate oxidase | EC 1.1.3.3 | (S)-malate |
| methanethiol oxidase | EC 1.8.3.4 | Methanethiol |
| monoamino acid oxidase | | |
| $N^6$-methyl-lysine oxidase | EC 1.5.3.4 | 6-N-methyl-L-lysine |
| N-acylhexosamine oxidase | EC 1.1.3.29 | N-acetyl-D-glucosamine N-glycolylglucosamine N-acetylgalactosamine N-acetylmannosamine. |
| NAD(P)H oxidase | EC 1.6.3.1 | NAD(P)H |
| nitroalkane oxidase | EC 1.7.3.1 | a nitroalkane |
| N-methyl-L-amino-acid oxidase | EC 1.5.3.2 | an N-methyl-L-amino acid |
| nucleoside oxidase | EC 1.1.3.39 | Adenosine |
| Oxalate oxidase | EC 1.2.3.4 | Oxalate |
| polyamine oxidase | EC 1.5.3.11 | 1-N-acetylspermine |
| polyphenol oxidase | EC 1.14.18.1 | |
| Polyvinyl-alcohol oxidase | EC 1.1.3.30 | polyvinyl alcohol |
| prenylcysteine oxidase | EC 1.8.3.5 | an S-prenyl-L-cysteine |
| Protein-lysine 6-oxidase | EC 1.4.3.13 | peptidyl-L-lysyl-peptide |
| putrescine oxidase | EC 1.4.3.10 | butane-1,4-diamine |

TABLE 1-continued

| ACCEPTED COMMON NAME | IUBMB ENZYME NOMENCLATURE | PREFERRED SUBSTRATE |
|---|---|---|
| Pyranose oxidase | EC 1.1.3.10 | D-glucose D-xylose L-sorbose D-glucono-1,5-lactone |
| Pyridoxal 5'-phosphate synthase | EC 1.4.3.5 | pyridoxamine 5'-phosphate |
| pyridoxine 4-oxidase | EC 1.1.3.12 | Pyridoxine |
| pyrroloquinoline-quinone synthase | EC 1.3.3.11 | 6-(2-amino-2-carboxyethyl)-7,8-dioxo-1,2,3,4,5,6,7,8-octahydroquinoline-2,4-dicarboxylate |
| Pyruvate oxidase | EC 1.2.3.3 | Pyruvate |
| Pyruvate oxidase (CoA-acetylating) | EC 1.2.3.6 | Pyruvate |
| Reticuline oxidase | EC 1.21.3.3 | Reticuline |
| retinal oxidase | EC 1.2.3.11 | Retinal |
| Rifamycin-B oxidase | EC 1.10.3.6 | rifamycin-B |
| Sarcosine oxidase | EC 1.5.3.1 | Sarcosine |
| secondary-alcohol oxidase | EC 1.1.3.18 | a secondary alcohol |
| sulfite oxidase | EC 1.8.3.1 | Sulfite |
| superoxide dismutase | EC 1.15.1.1 | Superoxide |
| superoxide reductase | EC 1.15.1.2 | Superoxide |
| tetrahydroberberine oxidase | EC 1.3.3.8 | (S)-tetrahydroberberine |
| Thiamine oxidase | EC 1.1.3.23 | Thiamine |
| tryptophan α,β-oxidase | EC 1.3.3.10 | L-tryptophan |
| urate oxidase (uricase, uric acid oxidase) | EC 1.7.3.3 | uric acid |
| Vanillyl-alcohol oxidase | EC 1.1.3.38 | vanillyl alcohol |
| Xanthine oxidase | EC 1.17.3.2 | Xanthine |
| xylitol oxidase | EC 1.1.3.41 | Xylitol | e) Autoantibody

As used herein, the phrase "autoantibody" refers to an antibody that binds to an analyte that is endogenously produced in the subject in which the antibody is produced.

f) n-capture Antibody: cTnT Complex $(C_1)(C_2) \ldots (C_n)$ (cTnT),

As used herein, the phrase "n-capture antibody: cTnT complex" refers to a combination of at least one antibody and cTnT, wherein the antibody and cTnT are bound by specific, noncovalent interactions between an antigen-combining site on the antibody and a cTnT epitope.

g) Detectable Label

As used herein the term "detectable label" refers to any moiety that generates a measurable signal via optical, electrical, or other physical indication of a change of state of a molecule or molecules coupled to the moiety. Such physical indicators encompass spectroscopic, photochemical, biochemical, immunochemical, electromagnetic, radiochemical, and chemical means, such as but not limited to fluorescence, chemifluorescence, chemiluminescence, and the like. Preferred detectable labels include acridinium compounds such as an acridinium-9-carboximide having a structure according to Formula I as set forth in section B herein below, and an acridinium-9-carboxylate aryl ester having a structure according to Formula II as also set forth in section B herein below.

h) Subject

As used herein, the terms "subject" and "patient" are used interchangeably irrespective of whether the subject has or is currently undergoing any form of treatment. As used herein, the terms "subject" and "subjects" refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous monkey, chimpanzee, etc) and a human). Preferably, the subject is a human.

i) Test Sample

As used herein, the term "test sample" generally refers to a biological material being tested for and/or suspected of containing an analyte of interest and which may also include autoantibodies to cTnT. The biological material may be derived from any biological source but preferably is a biological fluid likely to contain cTnT. Examples of biological materials include, but are not limited to, stool, whole blood, serum, plasma, red blood cells, platelets, interstitial fluid, saliva, ocular lens fluid, cerebral spinal fluid, sweat, urine, ascites fluid, mucous, nasal fluid, sputum, synovial fluid, peritoneal fluid, vaginal fluid, menses, amniotic fluid, semen, soil, etc. The test sample may be used directly as obtained from the biological source or following a pretreatment to modify the character of the sample. For example, such pretreatment may include preparing plasma from blood, diluting viscous fluids and so forth. Methods of pretreatment may also involve filtration, precipitation, dilution, distillation, mixing, concentration, inactivation of interfering components, the addition of reagents, lysing, etc. If such methods of pretreatment are employed with respect to the test sample, such pretreatment methods are such that cTnT remains in the test sample at a concentration proportional to that in an untreated test sample (e.g., namely, a test sample that is not subjected to any such pretreatment method(s)).

B. IMMUNOASSAY FOR DETECTING CTNT IN A TEST SAMPLE That May Contain Heterophilic Endogenous Antibodies, And Autoantibodies The present disclosure relates to an immunoassay for detecting cTnT in a test sample in which other substances that may interfere with immunodetection of cTnT may be present. Such substances include for example, heterophilic endogenous antibodies, and autoantibodies against cTnT. The immunoassay of the present disclosure involves obtaining a test sample from a subject and then detecting the presence of cTnT using immunodetection while compensating for the presence of any such substances that may be present in the sample. This is achieved in part by providing n capture antibodies (C) that bind to at least n epitopes on cTnT to form a n-capture antibody: cTnT complex $(C1)(C2) \ldots (Cn)(cTnT)$ wherein n is an integer from 1 to 10, and n' detection antibodies (D) that bind to n' epitopes on cTnT to form a n'-detection antibody: n-capture antibody: cTnT measurable assembly $(D_1)(D_2) \ldots (Dn') (C_1)(C_2) \ldots (Cn)(cTnT)$, wherein n' and n are independently an integer from 1 to 10, and antibodies C and D bind to (n+n') different epitopes of cTnT. In other words, each of n capture antibodies C binds to at least one epitope on cTnT, and each of n' detection antibodies D binds to at least one epitope on cTnT that is different than any of the epitopes to which any of the capture antibodies C bind. Typically the detection antibodies are labeled with a detectable label, which may be conjugated directly or indirectly to the detection antibodies. The antibodies can be provided, i.e. bound to a solid phase, which can be a solid support on which for example the capture antibodies are immobilized.

Immunoassay Methods

The immunoassay methods of the present disclosure can be carried out in any of a wide variety of formats. A general review of immunoassays is available in METHODS IN CELL BIOLOGY VOLUME 37: ANTIBODIES IN CELL BIOLOGY, Asai, ed. Academic Press, Inc. New York (1993), and BASIC AND CLINICAL IMMUNOLOGY 7 TH EDITION, Stites & Terr, eds. (1991), which are herein incorporated by reference in its entirety. A typical heterogeneous sandwich immunoassay employs a solid phase (as a solid support) to which is bound a first (capture) antibody reactive with at least one epitope on cTnT. A second (detection) antibody is also reactive with at least one epitope on cTnT. The second antibody may be conjugated to a detectable label that provides a signal that is measured after the detection antibody binds to the captured cTnT. When a test sample containing the cTnT contacts the first antibody, the first antibody captures the cTnT. The cTnT is contacted with the second antibody resulting in the formation of an immunodetection complex consisting of the first antibody, cTnT and second antibody, and the complex is bound to the solid phase. The signal generated by the second (detection) antibody is proportional to the concentration of the cTnT as determined by the rate of formation ($k_1$) of the immunodetection complex versus the rate of dissociation of the immunodetection complex ($k_2$). Heterophilic endogenous antibodies and any autoantibodies, which if present are unpredictable as to exactly where on cTnT they will bind, can substantially interfere with binding of the first and/or second antibody, and thus with the resulting signal.

In contrast to a typical immunoassay format, immunoassays according to an exemplary embodiment of the present disclosure employ multiple capture antibodies and/or multiple detection antibodies, wherein each detection antibody binds to at least one epitope on cTnT that is different than any of the epitopes to which any of the capture antibody or antibodies bind. It will be understood that the reference to "antibodies" in the plural, with respect to capture antibodies and detection antibodies, can refer to use in the immunoassay of one type of antibody, as in for example use of one capture antibody with use of multiple detection antibodies, or use of one detection antibody with use of multiple capture antibodies. In any case, the use of multiple capture and/or detection antibodies, wherein the capture antibodies used and detection antibodies used are distinguished by a lack of binding specificity for the same epitopes on cTnT, improves the specificity of the detection, improves the quality of signal and therefore its accuracy as to cTnT amount, and decreases noise in the signal from nonspecific binding due to the presence any heterophilic endogenous antibodies and/or autoantibodies. The signal generated by the detection antibodies remains proportional to the concentration of cTnT, but is determined by the rate of formation of a new immunodetection complex: n'-detection antibody: n-capture antibody: cTnT measurable assembly $(D_1)(D_2) \ldots (Dn') (C_1)(C_2) \ldots (Cn)(cTnT)$, versus the rate of dissociation of the new immunodetection complex. Use of more than one capture phase antibody and more than one detection antibody improves accuracy of the immunoassay by increasing the signal from specific binding to cTnT.

The methods also provide for the use of humanized immunoreagents, which overcomes any interference from heterophilic antibodies that may be present in the test sample. For example, the capture antibodies, the detection antibodies or both the capture and detection antibodies used may be humanized. Additionally, antihuman IgG antibody can be used for the detection antibodies to correct for endogenous autoantibodies to cTnT. For example, anti-human IgG may be complexed to humanized detection antibodies. A detectable label such as those described elsewhere herein, including any of the acridinium compounds described elsewhere herein, may then be conjugated to the anti-human IgG. Moreover, when used in conjunction with humanized immunoreagents, antihuman IgG provides a "universal" signal generator. Derivatized cTnT can be used to provide a soluble reagent suitable for assay standardization.

Thus, according to one embodiment, an immunoassay of the present disclosure to detect the presence of cTnT is a heterogeneous assay employing a solid phase, which can be a solid support. The immunoassay can be performed for example by immobilizing one or more capture antibodies $(C_1)(C_2) \ldots (Cn)$ on the solid phase, wherein each capture antibody Cn is an exogenous capture antibody, i.e. an exogenous antibody that is reactive with at least one epitope on cTnT. Under conditions sufficient for specific binding of each antibody Cn to cTnT, the test sample suspected of containing the cTnT and which may or may not contain other interfering substances, is contacted with the capture antibodies $(C_1)(C_2) \ldots (Cn)$, thus forming a n-capture antibody: cTnT complex $(C_1)(C_2) \ldots (Cn)(cTnT)$. The n-capture antibody: cTnT complex $(C_1)(C_2) \ldots (Cn)(cTnT)$ is contacted with n' detection antibodies (D) that bind to n' epitopes on cTnT to form a n'-detection antibody: n-capture antibody: cTnT measurable assembly $(D_1)(D_2) \ldots (Dn') (C_1)(C_2) \ldots (Cn)(cTnT)$. This step is carried out under conditions sufficient for specific binding of the D antibodies to any of the cTnT that is present in the test sample. By "measurable assembly" is meant a configuration of molecules that when formed generates a signal susceptible to physical detection and/or quantification. In certain embodiments for example, the detection antibodies D may be labeled with a detectable label. The label may be directly or indirectly conjugated to the detection antibodies. For example, in an exemplary embodiment, the detection antibodies are humanized and complexed to an antihuman IgG antibody, and then the detectable label s conjugated to the antihuman IgG antibody. Any detectable label may be conjugated to the antihuman IgG antibody, including any of the acridinium compounds described elsewhere herein. Depending on the detectable label selected and detection approach used, an optical, electrical, or change-of-state signal of the assembly is measured. Use of antihuman IgG antibody in the detection antibody corrects for endogenous autoantibodies to cTnT.

Although the immunoassay is described above as including a sequence of steps for illustrative purposes, the test sample may be contacted with the capture antibodies C and the detection antibodies D simultaneously or sequentially, in any order.

In one format of a sandwich immunoassay according to the present disclosure, detecting comprises detecting a signal from the solid phase-affixed immunodetection complex which is a n'-detection antibody: n-capture antibody: cTnT measurable assembly $(D_1)(D_2) \ldots (Dn') (C_1)(C_2) \ldots (Cn)$ (cTnT). In one embodiment, the immunodetection complex is separated from the solid phase, typically by washing, and the signal from the bound label is detected. In another format of a sandwich immunoassay according to the present disclosure, the immunodetection complex remains a solid phase-affixed complex, which is then detected.

Antibodies

In the immunoassays according to the present disclosure, each capture antibody C can be a polyclonal antibody, a monoclonal antibody, a chimeric antibody, a human antibody, an affinity maturated antibody or an antibody fragment. Similarly, each detection antibody D can be a polyclonal antibody, a monoclonal antibody, a chimeric antibody, a human antibody, an affinity maturated antibody or an antibody fragment.

In an exemplary embodiment of the immunoassays, the capture antibodies, the detection antibodies or both the capture antibodies and detection antibodies are humanized. In another exemplary embodiment, the detection antibodies are humanized and complexed to an antihuman IgG antibody. The detectable label may be conjugated to the antihuman IgG antibody.

While monoclonal antibodies are highly specific to the analyte/antigen, a polyclonal antibody can preferably be used as each capture antibody C to immobilize as much of the analyte/antigen as possible. A monoclonal antibody with inherently higher binding specificity for the analyte/antigen may then preferably be used for each detection antibody D. In any case, the capture and detection antibodies recognize non-overlapping epitopes on cTnT, and in an exemplary embodiment are capable of binding simultaneously to different epitopes on cTnT, each without interfering with the binding of the other.

Polyclonal antibodies are raised by injecting (e.g., subcutaneous or intramuscular injection) an immunogen into a suitable non-human mammal (e.g., a mouse or a rabbit). Generally, the immunogen should induce production of high titers of antibody with relatively high affinity for the target antigen.

If desired, the antigen may be conjugated to a carrier protein by conjugation techniques that are well known in the art. Commonly used carriers include keyhole limpet hemocyanin (KLH), thyroglobulin, bovine serum albumin (BSA), and tetanus toxoid. The conjugate is then used to immunize the animal.

The antibodies are then obtained from blood samples taken from the animal. The techniques used to produce polyclonal antibodies are extensively described in the literature (see, e.g., Methods of Enzymology, "Production of Antisera With Small Doses of Immunogen: Multiple Intradermal Injections," Langone, et al. eds. (Acad. Press, 1981)). Polyclonal antibodies produced by the animals can be further purified, for example, by binding to and elution from a matrix to which the target antigen is bound. Those of skill in the art will know of various techniques common in the immunology arts for purification and/or concentration of polyclonal, as well as monoclonal, antibodies (see, e.g., Coligan, et al. (1991) Unit 9, Current Protocols in Immunology, Wiley Interscience).

For many applications, monoclonal antibodies (mAbs) are preferred. The general method used for production of hybridomas secreting mAbs is well known (Kohler and Milstein (1975) Nature, 256:495). Briefly, as described by Kohler and Milstein, the technique entailed isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody that bound to cancer cell lines. Confirmation of specificity among mAbs can be accomplished using routine screening techniques (such as the enzyme-linked immunosorbent assay, or "ELISA") to determine the elementary reaction pattern of the mAb of interest.

As used herein, the term "antibody" encompasses antigen-binding antibody fragments, e.g., single chain antibodies (scFv or others), which can be produced/selected using phage display technology. The ability to express antibody fragments on the surface of viruses that infect bacteria (bacteriophage or phage) makes it possible to isolate a single binding antibody fragment, e.g., from a library of greater than $10^{10}$ nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) Nature, 348: 552-554; Hoogenboom et al. (1991) Nucleic Acids Res. 19: 4133-4137).

Since the antibody fragments on the surface of the phage are functional, phage-bearing antigen-binding antibody fragments can be separated from non-binding phage by antigen affinity chromatography (McCafferty et al. (1990) Nature, 348: 552-554). Depending on the affinity of the antibody fragment, enrichment factors of 20-fold-1,000,000-fold are obtained for a single round of affinity selection. By infecting bacteria with the eluted phage, however, more phage can be grown and subjected to another round of selection. In this way, an enrichment of 1000-fold in one round can become 1,000,000-fold in two rounds of selection (McCafferty et al. (1990) Nature, 348: 552-554). Thus, even when enrichments are low (Marks et al. (1991) J. Mol. Biol. 222: 581-597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen. Human antibodies can be produced without prior immunization by displaying very large and diverse V-gene repertoires on phage (Marks et al. (1991) J. Mol. Biol. 222: 581-597). In one embodiment, natural VH and VL repertoires present in human peripheral blood lymphocytes are isolated from unimmunized donors by PCR. The V-gene repertoires can be spliced together at random using PCR to create a scFv gene repertoire which can be cloned into a phage vector to create a library of 30 million phage antibodies (Id.). From a single "naive" phage antibody library, binding antibody fragments have been isolated against more than 17 different antigens, including haptens, polysaccharides, and proteins (Marks et al. (1991) J. Mol. Biol. 222: 581-597; Marks et al. (1993). Bio/Technology. 10: 779-783; Griffiths et al. (1993) EMBO J. 12: 725-734; Clackson et al. (1991) Nature. 352: 624-628). Antibodies have been produced against self proteins, including human thyroglobulin, immunoglobulin, tumor necrosis factor, and CEA (Griffiths et al. (1993) EMBO J. 12: 725-734). The antibody fragments are highly specific for the antigen used for selection and have affinities in the 1 nM to 100 nM range (Marks et al. (1991) J. Mol. Biol. 222: 581-597; Griffiths et al. (1993)

EMBO J. 12: 725-734). Larger phage antibody libraries result in the isolation of more antibodies of higher binding affinity to a greater proportion of antigens.

As those of skill in the art readily appreciate, antibodies can be prepared by any of a number of commercial services (e.g., Berkeley Antibody Laboratories, Bethyl Laboratories, Anawa, Eurogenetec, etc.).

Solid Phase

A solid phase can be any suitable material with sufficient surface affinity to bind an antibody, for example each capture antibody C. The solid phase can take any of a number of forms, such as a magnetic particle, bead, test tube, microtiter plate, cuvette, membrane, a scaffolding molecule, quartz crystal, film, filter paper, disc or a chip. Useful solid phase materials include: natural polymeric carbohydrates and their synthetically modified, crosslinked, or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, tubes, particulates, or plates, or they may be coated onto, bonded, or laminated to appropriate inert carriers, such as paper, glass, plastic films, fabrics, or the like. Nitrocellulose has excellent absorption and adsorption qualities for a wide variety of reagents including monoclonal antibodies. Nylon also possesses similar characteristics and also is suitable.

Alternatively, the solid phase can constitute microparticles. Microparticles useful in the present disclosure can be selected by one skilled in the art from any suitable type of particulate material and include those composed of polystyrene, polymethylacrylate, polypropylene, latex, polytetrafluoroethylene, polyacrylonitrile, polycarbonate, or similar materials. Further, the microparticles can be magnetic or paramagnetic microparticles, so as to facilitate manipulation of the microparticle within a magnetic field. In an exemplary embodiment the microparticles are carboxylated magnetic microparticles.

Microparticles can be suspended in the mixture of soluble reagents and test sample or can be retained and immobilized by a support material. In the latter case, the microparticles on or in the support material are not capable of substantial movement to positions elsewhere within the support material. Alternatively, the microparticles can be separated from suspension in the mixture of soluble reagents and test sample by sedimentation or centrifugation. When the microparticles are magnetic or paramagnetic the microparticles can be separated from suspension in the mixture of soluble reagents and test sample by a magnetic field.

The methods of the present disclosure can be adapted for use in systems that utilize microparticle technology including automated and semi-automated systems wherein the solid phase comprises a microparticle. Such systems include those described in pending U.S. application Ser. No. 425,651 and U.S. Pat. No. 5,089,424, which correspond to published EPO App. Nos. EP 0 425 633 and EP 0 424 634, respectively, and U.S. Pat. No. 5,006,309.

In particular embodiments, the solid phase includes one or more electrodes. Capture antibodies C can be affixed for example, directly or indirectly, to the electrode(s). In one embodiment, for example, capture antibodies C can be affixed to magnetic or paramagnetic microparticles, which are then positioned in the vicinity of the electrode surface using a magnet. Systems in which one or more electrodes serve as the solid phase are useful where detection is based on electrochemical interactions. Exemplary systems of this type are described, for example, in U.S. Pat. No. 6,887,714 (issued May 3, 2005). The basic method is described further below with respect to electrochemical detection.

The capture antibodies C can be attached to the solid phase by adsorption, where they are retained by hydrophobic forces. Alternatively, the surface of the solid phase can be activated by chemical processes that cause covalent linkage of the capture antibodies to the support.

To change or enhance the intrinsic charge of the solid phase, a charged substance can be coated directly onto the solid phase. Ion capture procedures for immobilizing an immobilizable reaction complex with a negatively charged polymer, described in U.S. application Ser. No. 150,278, corresponding to EP Publication No. 0326100, and U.S. application Ser. No. 375,029 (EP Publication No. 0406473), can be employed according to the present disclosure to affect a fast solution-phase immunochemical reaction. In these procedures, an immobilizable immune complex is separated from the rest of the reaction mixture by ionic interactions between the negatively charged polyanion/immune complex and the previously treated, positively charged matrix and detected by using any of a number of signal-generating systems, including, e.g., chemiluminescent systems, as described in U.S. application Ser. No. 921,979, corresponding to EPO Publication No. 0 273,115.

If the solid phase is silicon or glass, the surface must generally be activated prior to attaching each capture antibody C. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercapto-propyl)-trimethoxy silane (Sigma Chemical Co., St. Louis, Mo.) can be used to introduce reactive groups such as amino-, vinyl, and thiol, respectively. Such activated surfaces can be used to link the capture directly (in the cases of amino or thiol), or the activated surface can be further reacted with linkers such as glutaraldehyde, bis(succinimidyl) suberate, SPPD 9 succinimidyl 3-[2-pyridyldithio]propionate), SMCC (succinimidyl-4-[Nmaleimidomethyl]cyclohexane-1-carboxylate), SIAB (succinimidyl[4iodoacetyl]aminobenzoate), and SMPB (succinimidyl 4-[1maleimidophenyl]butyrate) to separate the capture antibody from the surface. Vinyl groups can be oxidized to provide a means for covalent attachment. Vinyl groups can also be used as an anchor for the polymerization of various polymers such as poly-acrylic acid, which can provide multiple attachment points for specific capture antibodies. Amino groups can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia, Piscataway, N.J.), or Ficoll (molecular weight 70,000 daltons; available from Sigma Chemical Co., St. Louis, Mo.). Additionally, polyelectrolyte interactions can be used to immobilize a specific capture antibody on a solid phase using techniques and chemistries described U.S. application Ser. No. 150,278, filed Jan. 29, 1988, and U.S. application Ser. No. 375,029, filed Jul. 7, 1989, each of which is incorporated herein by reference.

Other considerations affecting the choice of solid phase include the ability to minimize non-specific binding of labeled entities and compatibility with the labeling system employed. For, example, solid phases used with fluorescent labels should have sufficiently low background fluorescence to allow signal detection.

Following attachment of a specific capture antibody, the surface of the solid support may be further treated with materials such as serum, proteins, or other blocking agents to minimize non-specific binding.

Detection Systems in General

As discussed above, immunoassays according to the present disclosure employ one or more detection antibodies D, each of which is cTnT-specific. In certain embodiments, each detection antibody D has a detectable label.

Detectable labels suitable for use in the detection antibodies of the present disclosure include any compound or composition having a moiety that is detectable by spectroscopic, photochemical, biochemical, immunochemical, electrical, optical, or chemical means. Such labels include, for example, an enzyme, oligonucleotide, nanoparticle chemiluminophore, fluorophore, fluorescence quencher, chemiluminescence quencher, or biotin. Thus for example, in an immunoassay employing an optical signal, the optical signal is measured as an analyte concentration dependent change in chemiluminescence, fluorescence, phosphorescence, electrochemiluminescence, ultraviolet absorption, visible absorption, infrared absorption, refraction, surface plasmon resonance. In an immunoassay employing an electrical signal, the electrical signal is measured as an analyte concentration dependent change in current, resistance, potential, mass to charge ratio, or ion count. In an immunoassay employing a change-of-state signal, the change of state signal is measured as an analyte concentration dependent change in size, solubility, mass, or resonance.

Useful labels according to the present disclosure include magnetic beads (e.g., Dynabeads™), fluorescent dyes (e.g., fluorescein, Texas Red, rhodamine, green fluorescent protein) and the like (see, e.g., Molecular Probes, Eugene, Oreg., USA), chemiluminescent compounds such as acridinium (e.g., acridinium-9-carboxamide), phenanthridinium, dioxetanes, luminol and the like, radiolabels (e.g., $^3$H, $^{125}$I, $^{35}$S, $^{14}$C, or $^{32}$P), catalysts such as enzymes (e.g., horse radish peroxidase, alkaline phosphatase, beta-galactosidase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277, 437; 4,275,149; and 4,366,241.

The label can be attached to each detection antibody prior to, or during, or after contact with the biological sample. So-called "direct labels" are detectable labels that are directly attached to or incorporated into the detection antibody prior to use in the assay. Direct labels can be attached to or incorporated into the detection antibody by any of a number of means well known to those of skill in the art.

In contrast, so-called "indirect labels" typically bind to each detection antibody at some point during the assay. Often, the indirect label binds to a moiety that is attached to or incorporated into the detection agent prior to use. Thus, for example, each detection antibody can be biotinylated before use in an assay. During the assay, an avidin-conjugated fluorophore can bind the biotin-bearing detection agent, to provide a label that is easily detected.

In another example of indirect labeling, polypeptides capable of specifically binding immunoglobulin constant regions, such as polypeptide A or polypeptide G, can also be used as labels for detection antibodies. These polypeptides are normal constituents of the cell walls of streptococcal bacteria. They exhibit a strong non-immunogenic reactivity with immunoglobulin constant regions from a variety of species (see, generally Kronval, et al. (1973) J. Immunol., 111: 1401-1406, and Akerstrom (1985) J. Immunol., 135: 2589-2542). Such polypeptides can thus be labeled and added to the assay mixture, where they will bind to each capture and detection antibody, as well as to the autoantibodies, labeling all and providing a composite signal attributable to analyte and autoantibody present in the sample.

Some labels useful in the present disclosure may require the use of an additional reagent(s) to produce a detectable signal. In an ELISA, for example, an enzyme label (e.g., beta-galactosidase) will require the addition of a substrate (e.g., X-gal) to produce a detectable signal. In immunoassays using an acridinium compound as the direct label, a basic solution and a source of hydrogen peroxide are added.

Detection Systems—Exemplary Formats

Chemiluminescence Immunoassay: In an exemplary embodiment, a chemiluminescent compound is used in the above-described methods as a direct label conjugated to each detection antibody D. The chemiluminescent compound can be an acridinium compound. When an acridinium compound is used as the detectable label, then the above-described method may further include generating or providing a source of hydrogen peroxide to the mixture resulting from contacting the test sample with the first antibody and the second antibody, and adding at least one basic solution to the mixture to generate a light signal. The light signal generated or emitted by the mixture is then measured to detect cTnT in the test sample.

The source of hydrogen peroxide may be a buffer solution or a solution containing hydrogen peroxide or an enzyme that generates hydrogen peroxide when added to the test sample. The basic solution serves as a trigger solution, and the order in which the at least one basic solution and detectable label are added is not critical. The basic solution used in the method is a solution that contains at least one base and that has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate and calcium bicarbonate. The amount of basic solution added to the test sample depends on the concentration of the basic solution used in the assay. Based on the concentration of the basic solution used, one skilled in the art could easily determine the amount of basic solution to be used in the method described herein.

In a chemiluminescence immunoassay according to the present disclosure and using an acridinium compound as the detectable label, preferably the acridinium compound is an acridinium-9-carboxamide. Specifically, the acridinium-9-carboxamide has a structure according to formula I:

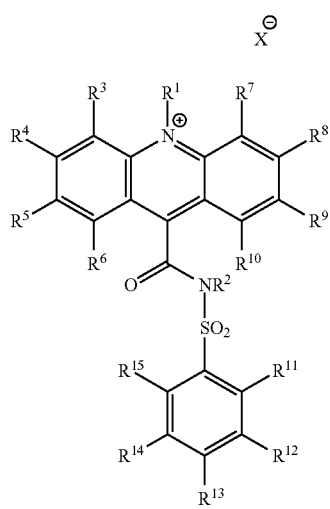

I wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and further wherein any of the alkyl, alkenyl, alkynyl, aryl or aralkyl may contain one or more heteroatoms; and optionally, if present, $X^{\ominus}$ is an anion.

Methods for preparing acridinium 9-carboxamides are described in Mattingly, P. G. *J. Biolumin. Chemilumin.*, 6, 107-14; (1991); Adamczyk, M.; Chen, Y.-Y., Mattingly, P. G.; Pan, Y. J. Org. Chem., 63, 5636-5639 (1998); Adamczyk, M.; Chen, Y.-Y.; Mattingly, P. G.; Moore, J. A.; Shreder, K. *Tetrahedron*, 55, 10899-10914 (1999); Adamczyk, M.; Mattingly, P. G.; Moore, J. A.; Pan, Y. *Org. Lett.*, 1, 779-781 (1999); Adamczyk, M.; Chen, Y.-Y.; Fishpaugh, J. R.; Mattingly, P. G.; Pan, Y.; Shreder, K.; Yu, Z. *Bioconjugate Chem.*, 11, 714-724 (2000); Mattingly, P. G.; Adamczyk, M. In *Luminescence Biotechnology: Instruments and Applications*; Dyke, K. V. Ed.; CRC Press: Boca Raton, pp. 77-105 (2002); Adamczyk, M.; Mattingly, P. G.; Moore, J. A.; Pan, Y. *Org. Lett.*, 5, 3779-3782 (2003); and U.S. Pat. Nos. 5,468,646, 5,543,524 and 5,783,699 (each incorporated herein by reference in their entireties for their teachings regarding same).

Alternatively, the acridinium compound can be an acridinium-9-carboxylate aryl ester; the acridinium-9-carboxylate aryl ester can have a structure according to formula II:

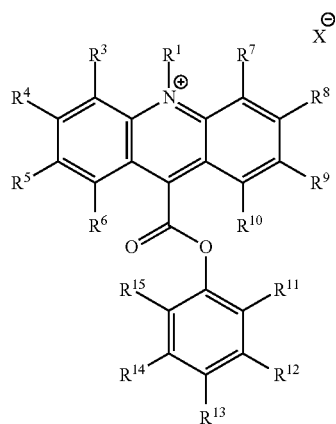

II wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^{\ominus}$ is an anion.

Examples of acridinium-9-carboxylate aryl esters having the above formula II that can be used in the present disclosure include, but are not limited to, 10-methyl-9-(phenoxycarbonyl)acridinium fluorosulfonate (available from Cayman Chemical, Ann Arbor, Mich.). Methods for preparing acridinium 9-carboxylate aryl esters are described in McCapra, F., et al., *Photochem. Photobiol.*, 4, 1111-21 (1965); Razavi, Z et al., *Luminescence*, 15:245-249 (2000); Razavi, Z et al., *Luminescence*, 15:239-244 (2000); and U.S. Pat. No. 5,241,070 (each incorporated herein by reference in their entireties for their teachings regarding same).

In addition to the at least one acridinium compound, the indicator solution can also contain at least one surfactant. Any surfactant that when dissolved in water, lowers the surface tension of the water and increases the solubility of organic compounds, can be used in the present invention. Examples of surfactants that can be used is one or more non-ionic or ionic surfactants (e.g., anionic, cationic or zwitterionic surfactants). Examples of non-ionic surfactants that can be used include, but are not limited to, t-octylpheoxypolyethoxyethanol (TRITON X-100, Sigma Aldrich, St. Louis, Mo.), polyoxyethylenesorbitan monolaurate (Tween 20), nonylphenol polyoxyethylene ether (Nonidet P10), decyldimethylphosphine oxide (APO-10), Cyclohexyl-n-ethyl-β-D-Maltoside, Cyclohexyl-n-hexyl-β-D-Maltoside, Cyclohexyl-n-methyl-β-D-Maltoside, n-Decanoylsucrose, n-Decyl-β-D-glucopyranoside, n-Decyl-β-D-maltopyranoside, n-Decyl-β-D-thiomaltoside, Digitonin, n-Dodecanoyl sucrose, n-Dodecyl-β-D-glucopyranoside, n-Dodecyl-β-D-maltoside, polyoxyethylene (10) dodecyl ether (Genapol C-100), isotridecanol polyglycol ether (Genapol X-80), isotridecanol polyglycol ether (Genapol X-100), Heptane-1,2,3-triol, n-Heptyl-β-D-glucopyranoside, n-Heptyl-β-D-thioglucopyranoside and combinations thereof. An example of a ionic surfactant that can be used include, sodium cholate, chenodeoxycholic acid, cholic acid, dehydrocholic acid, docusate sodium, docusate sodium salt, glycocholic acid hydrate, glycodeoxycholic acid monohydrate, glycolithocholic acid ethyl ester, N-lauroylsarcosine sodium salt, N-lauroylsarcosine, lithium dodecyl sulfate, calcium propionate, 1-octanesulfonic acid sodium salt, sodium 1-butanesulfonate, sodium chenodeoxycholate, sodium cholate hydrate, sodium 1-decanesulfonate, sodium 1-decanesulfonate, sodium deoxycholate, sodium deoxycholate monohydrate, sodium dodecylbenzenesulfonate, sodium dodecyl sulfate, sodium glycochenodeoxycholate, sodium glycocholate hydrate, sodium 1-heptanesulfonate, sodium hexanesulfonate, sodium 1-nonanesulfonate, sodium octyle sulfate, sodium pentanesulfonate, sodium 1-propanesulfonate hydrate, sodium taurodeoxycholate hydrate, sodium taurohyodeoxycholate hydrate, sodium tauroursodeoxycholate, taurocholic acid sodium salt hydrate, taurolithocholic acid 3-sulfate disodium salt, Triton® X-200, Triton® QS-15, Triton® QS-44, Triton® XQS-20, Trizma® dodecyl sulfate, ursodeoxycholic acid, alkyltrimethylammonium bromide, amprolium hydrocholoride, benzalkonium chloride, benzethonium hydroxide, benzyldimethylhexadecylammonium chloride, benzyldodecyldimethylammonium bromide, choline p-toluenesulfonate salt, dimethyldioctadecylammonium bromide, dodecylethyldimethylammonium bromide, dodecyltrimethylammonium bromide, ethylhexadecyldimethylammonium bromide, Ggirard's reagent, hexadecylpyridinium bromide, hexadecylpyridinium chloride monohydrate, hexadecylpyridinium chloride monohydrate, hexadecyltrimethylammonium bromide, hexadecyltrimethylammonium p-toluenesulfonate, hexadecyltrimethylammonium bromide, hexadecyltrimethylammonium p-toluenesulfonate, Hyamine® 1622, methylbenzethonium chloride, myristyltrimethylammonium bromide, oxyphenonium bromide, N,N',N'-polyoxyethylene (10)-N-tallow-1,3-diaminopropane, tetraheptylammonium bromide, tetrakis(decyl)ammonium bromide, thonzonium bromide and Luviquat™ FC370, Luviquat™ HM 552, Luviquat™ HOLD, Luviquat™ MS 370, Luviquat™ PQ 11PN and combinations thereof (all available from Sigma Aldrich, St. Louis, Mo.).

Optionally, the test sample may be treated prior to the addition of any one or more of the at least one basic solution, hydrogen peroxide source and detectable label. Such treatment may include dilution, ultrafiltration, extraction, precipitation, dialysis, chromatography and digestion. Such treatment may be in addition to and separate from any pretreatment that the test sample may receive or be subjected to as discussed previously herein. Moreover, if such treatment methods are employed with respect to the test sample, such treatment methods are such that cTnT remains in the test sample at a concentration proportional to that in an untreated test sample (e.g., namely, a test sample that is not subjected to any such treatment method(s)).

As mentioned briefly previously herein, the time and order in which the test sample, the at least one basic solution, source of hydrogen peroxide and the detectable label are added to form a mixture is not critical. Additionally, the mixture formed by the at least one basic solution, hydrogen peroxide source and the detectable label, can optionally be allowed to incubate for a period of time. For example, the mixture can be allowed to incubate for a period of time of from about 1 second to about 60 minutes. Specifically, the mixture can be allowed to incubate for a period of from about 1 second to about 18 minutes.

When a chemiluminescent detectable label is used, after the addition of the at least one basic solution, hydrogen peroxide source, and the detectable label to the test sample, a detectable signal, namely, a chemiluminescent signal, is generated. The signal generated by the mixture is detected for a fixed duration of time. Preferably, the mixture is formed and the signal is detected concurrently. The duration of the detection may range from about 0.01 to about 360 seconds, more preferably from about 0.1 to about 30 seconds, and most preferably from about 0.5 to about 5 seconds. Chemiluminescent signals generated can be detected using routine techniques known to those skilled in the art.

Thus, in a chemiluminescent immunoassay according to the present disclosure, a chemiluminescent detectable label is used and added to the test sample, the chemiluminescent signal generated after the addition of the basic solution and the detectable label indicates the presence of cTnT in the test sample, which signal can be detected. The amount or concentration of cTnT in the test sample can be quantified based on the intensity of the signal generated. Specifically, the amount of cTnT contained in a test sample is proportional to the intensity of the signal generated. Specifically, the amount of cTnT present can be quantified based on comparing the amount of light generated to a standard curve for cTnT or by comparison to a cTnT reference standard. The cTnT reference standard may comprise, for example, an anti-idiotypic antibody. The cTnT reference standard may comprise for example a derivatized cTnT, such as for example cTnT derivatized with a polyethylene glycol. The standard curve can be generated using serial dilutions or solutions to cTnT of known concentration, by mass spectroscopy, gravimetrically and by other techniques known in the art. The above kit may further comprise a cTnT reference standard.

Fluorescence Polarization Immunoassay (FPIA): In an exemplary embodiment, a fluorescent label is employed in a fluorescence polarization immunoassay (FPIA) according to the invention. Generally, fluorescent polarization techniques are based on the principle that a fluorescent label, when excited by plane-polarized light of a characteristic wavelength, will emit light at another characteristic wavelength (i.e., fluorescence) that retains a degree of the polarization relative to the incident light that is inversely related to the rate of rotation of the label in a given medium. As a consequence of this property, a label with constrained rotation, such as one bound to another solution component with a relatively lower rate of rotation, will retain a relatively greater degree of polarization of emitted light than when free in solution.

This technique can be employed in immunoassays according to the invention, for example, by selecting reagents such that binding of the fluorescently labeled entities forms a complex sufficiently different in size such that a change in the intensity light emitted in a given plane can be detected. For example, when a labeled cardiac troponin antibody is bound by one or more cardiac troponin antigens captured by the capture antibody and/or autoantibodies reactive with the cardiac troponin, the resulting complex is sufficiently larger, and its rotation is sufficiently constrained, relative to the free labeled cardiac troponin antibody that binding is easily detected.

Fluorophores useful in FPIA include fluorescein, aminofluorescein, carboxyfluorescein, and the like, preferably 5 and 6-aminomethylfluorescein, 5 and 6-aminofluorescein, 6-carboxyfluorescein, 5-carboxyfluorescein, thioureafluorescein, and methoxytriazinolyl-aminofluorescein, and similar fluorescent derivatives. Examples of commercially available automated instruments with which fluorescence polarization assays can be conducted include: the IMx system, the TDx system, and TDxFLx system (all available from Abbott Laboratories, Abbott Park, Ill.).

Scanning Probe Microscopy (SPM): The use of scanning probe microscopy (SPM) for immunoassays also is a technology to which the immunoassay methods of the present disclosure are easily adaptable. In SPM, in particular in atomic force microscopy, the capture antibody is affixed to the solid phase that in addition to being capable of binding autoantibodies, has a surface suitable for scanning. The capture antibody can, for example, be adsorbed to a plastic or metal surface. Alternatively, the capture antibody can be covalently attached to, e.g., derivatized plastic, metal, silicon, or glass according to methods known to those of ordinary skill in the art. Following attachment of the capture antibody, the test sample is contacted with the solid phase, and a scanning probe microscope is used to detect and quantify solid phase-affixed complexes. The use of SPM eliminates the need for labels that are typically employed in immunoassay systems. Such a system is described in U.S. App. No. 662,147, which is incorporated herein by reference.

MicroElectroMechanical Systems (MEMS): Immunoassays according to the present disclosure can also be carried out using a MicroElectroMechanical System (MEMS). MEMS are microscopic structures integrated onto silicon that combine mechanical, optical, and fluidic elements with electronics, allowing convenient detection of an analyte of interest. An exemplary MEMS device suitable for use in the present disclosure is the Protiveris' multicantilever array. This array is based on chemo-mechanical actuation of specially designed silicon microcantilevers and subsequent optical detection of the microcantilever deflections. When coated on one side with a binding partner, a microcantilever will bend when it is exposed to a solution containing the complementary molecule. This bending is caused by the change in the surface energy due to the binding event. Optical detection of the degree of bending (deflection) allows measurement of the amount of complementary molecule bound to the microcantilever.

Electrochemical Detection Systems: In other embodiments, immunoassays according to the present disclosure are carried out using electrochemical detection, the techniques for which are well known to those skilled in the art. Such electrochemical detection often employs one or more electrodes connected to a device that measures and records an electrical current. Such techniques can be realized in a number of commercially available devices, such as the I-STAT® (Abbott Laboratories, Abbott Park, Ill.) system, which comprises a hand-held electrochemical detection instrument and self-contained assay-specific reagent cartridges. For example, in the present invention, the basic trigger solution could be contained in the self-contained hemoglobin reagent cartridge and upon addition of the test sample, a current would be generated at least one electrode that is proportional to the amount of hemoglobin in the test sample. A basic procedure for electrochemical detection has been described for example by Heineman and coworkers. This entailed immobilization of a primary antibody (Ab, rat-anti mouse IgG), followed by exposure to a sequence of solutions containing the antigen (Ag, mouse IgG), the secondary antibody conjugated to an enzyme label (AP-Ab, rat anti mouse IgG and alkaline phosphatase), and p-aminophenyl phosphate (PAPP). The AP converts PAPP to p-aminophenol ($PAP_R$, the "R" is intended to distinguish the reduced form from the oxidized form, $PAP_O$, the quinoneimine), which is electrochemically reversible at potentials that do not interfere with reduction of oxygen and water at pH 9.0, where AP exhibits optimum activity. $PAP_R$ does not cause electrode fouling, unlike phenol whose precursor, phenylphosphate, is often used as the enzyme substrate. Although $PAP_R$ undergoes air and light oxidation, these are easily prevented on small scales and short time frames. Picomole detection limits for $PAP_R$ and femtogram detection limits for IgG achieved in microelectrochemical immunoassays using PAPP volumes ranging from 20 μl to 360 μL have been reported previously. In capillary immunoassays with electrochemical detection, the lowest detection limit reported thus far is 3000 molecules of mouse IgG using a volume of 70 μL and a 30 min or 25 min assay time.

In an exemplary embodiment employing electrochemical detection according to the present disclosure, a capture antibody reactive with cTnT can be immobilized on the surface of an electrode which is the solid phase. The electrode is then contacted with a test sample from, e.g., a human. Any analyte in the sample binds to the capture antibody to form a first solid phase-affixed complex. Autoantibodies also bind to the surface of the electrode thereby becoming immobilized on the surface of the electrode. Analyte in the test sample that is unbound by the capture antibody binds to immobilized autoantibodies that are reactive with the analyte to form a second solid phase-affixed complex. These solid phase-affixed complexes are contacted with a detection antibody that is analyte-specific and has a detectable label. Formation of an immunodetection complex including the first antibody-analyte-second antibody complex plus the autoantibody-analyte-second antibody complex results in generation of a signal by the detectable label, which is then detected.

Various electrochemical detection systems are described in U.S. Pat. No. 7,045,364 (issued May 16, 2006; incorporated herein by reference), U.S. Pat. No. 7,045,310 (issued May 16, 2006; incorporated herein by reference), U.S. Pat. No. 6,887,714 (issued May 3, 2005; incorporated herein by reference), U.S. Pat. No. 6,682,648 (issued Jan. 27, 2004; incorporated herein by reference); U.S. Pat. No. 6,670,115 (issued Dec. 30, 2003; incorporated herein by reference).

C. KITS

The present disclosure also provides kits for assaying test samples for presence of cTnT wherein the test sample may contain other substances that interfere with immunodetection of cTnT. Kits according to the present disclosure include one or more reagents useful for practicing one or more immunoassays according to the present disclosure. A kit generally includes a package with one or more containers holding the reagents, as one or more separate compositions or, optionally, as admixture where the compatibility of the reagents will allow. The test kit can also include other material(s), which may be desirable from a user standpoint, such as a buffer(s), a diluent(s), a standard(s), and/or any other material useful in sample processing, washing, or conducting any other step of the assay.

In certain embodiments, a test kit includes a humanized monoclonal antibody, wherein the humanized monoclonal antibody is specific for cTnT. This component can be used as a positive control in immunoassays according to the invention. If desired, this component can be included in the test kit in multiple concentrations to facilitate the generation of a standard curve to which the signal detected in the test sample can be compared. Alternatively, a standard curve can be generated by preparing dilutions of a single humanized monoclonal antibody solution provided in the kit.

Kits according to the present disclosure can include one or more capture antibodies C, each of which binds to at least one epitope on cTnT, and one or more detection antibodies D, each of which binds to at least one epitope on cTnT that is different from any epitope to which any of the capture antobodies bind, and instructions for detecting or quantifying cTnT. In certain embodiments test kits according to the present disclosure may include the solid phase, to which the capture antibodies and/or detection antibodies are bound. The solid phase may be a material such as a magnetic particle, a bead, a test tube, a microtiter plate, a cuvette, a membrane, a scaffolding molecule, a quartz crystal, a film, a filter paper, a disc or a chip.

Test kits according to the present disclosure can include for example non-human monoclonal antibodies against cTnT, as the capture and detection antibodies. The kit may also include a detectable label that can be or is conjugated to each detection antibody. In certain embodiments, the test kit includes at least one direct label, which may be an enzyme, oligonucleotide, nanoparticle chemiluminophore, fluorophore, fluorescence quencher, chemiluminescence quencher, or biotin. In some embodiments, the direct label is an acridinium compound such as an acridinium-9-carboxamide according to formula I:

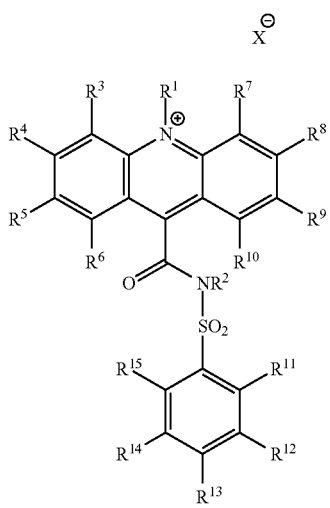

I wherein $R^1$ and $R^2$ are each independently selected from the group consisting of: alkyl, alkenyl, alkynyl, aryl or aralkyl, sulfoalkyl, carboxyalkyl and oxoalkyl, and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\ominus$ is an anion.

Alternatively, the acridinium compound can be an acridinium-9-carboxylate aryl ester having a structure according to formula II:

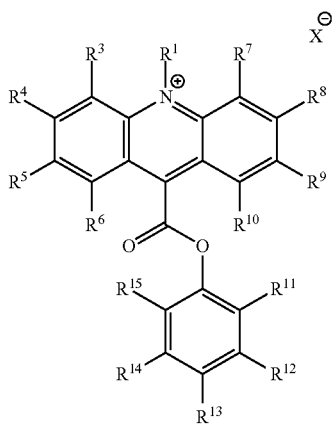

II wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\ominus$ is an anion.

Test kits according to the present disclosure and which include an acridinium compound can also include a basic solution. For example, the basic solution can be a solution having a pH of at least about 10.

In certain embodiments, test kits according to the present disclosure may further include a hydrogen peroxide source, such as a buffer solution, a solution containing hydrogen peroxide, or a hydrogen peroxide generating enzyme. For example, test kits may include an amount of a hydrogen peroxide generating enzymes selected from the following: (R)-6-hydroxynicotine oxidase, (S)-2-hydroxy acid oxidase, (S)-6-hydroxynicotine oxidase, 3-aci-nitropropanoate oxidase, 3-hydroxyanthranilate oxidase, 4-hydroxymandelate oxidase, 6-hydroxynicotinate dehydrogenase, abscisic-aldehyde oxidase, acyl-CoA oxidase, alcohol oxidase, aldehyde oxidase, amine oxidase, amine oxidase (copper-containing), amine oxidase (flavin-containing), aryl-alcohol oxidase, aryl-aldehyde oxidase, catechol oxidase, cholesterol oxidase, choline oxidase, columbamine oxidase, cyclohexylamine oxidase, cytochrome c oxidase, D-amino-acid oxidase, D-arabinono-1,4-lactone oxidase, D-arabinono-1,4-lactone oxidase, D-aspartate oxidase, D-glutamate oxidase, D-glutamate(D-aspartate) oxidase, dihydrobenzophenanthridine oxidase, dihydroorotate oxidase, dihydrouracil oxidase, dimethylglycine oxidase, D-mannitol oxidase, ecdysone oxidase, ethanolamine oxidase, galactose oxidase, glucose oxidase, glutathione oxidase, glycerol-3-phosphate oxidase, glycine oxidase, glyoxylate oxidase, hexose oxidase, hydroxyphytanate oxidase, indole-3-acetaldehyde oxidase, lactic acid oxidase, L-amino-acid oxidase, L-aspartate oxidase, L-galactonolactone oxidase, L-glutamate oxidase, L-gulonolactone oxidase, L-lysine 6-oxidase, L-lysine oxidase, long-chain-alcohol oxidase, L-pipecolate oxidase, L-sorbose oxidase, malate oxidase, methanethiol oxidase, monoamino acid oxidase, N6-methyl-lysine oxidase, N-acylhexosamine oxidase, NAD(P)H oxidase, nitroalkane oxidase, N-methyl-L-amino-acid oxidase, nucleoside oxidase, oxalate oxidase, polyamine oxidase, polyphenol oxidase, polyvinyl-alcohol oxidase, prenylcysteine oxidase, protein-lysine 6-oxidase, putrescine oxidase, pyranose oxidase, pyridoxal 5'-phosphate synthase, pyridoxine 4-oxidase, pyrroloquinoline-quinone synthase, pyruvate oxidase, pyruvate oxidase (CoA-acetylating), reticuline oxidase, retinal oxidase, rifamycin-B oxidase, sarcosine oxidase, secondary-alcohol oxidase, sulfite oxidase, superoxide dismutase, superoxide reductase, tetrahydroberberine oxidase, thiamine oxidase, tryptophan α,β-oxidase, urate oxidase (uricase, uric acid oxidase), vanillyl-alcohol oxidase, xanthine oxidase, xylitol oxidase and combinations thereof.

Test kits according to the present disclosure preferably include instructions for carrying out one or more of the immunoassays of the invention. Instructions included in kits of the present disclosure can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

D. ADAPTATIONS OF THE METHODS OF THE PRESENT DISCLOSURE

The present disclosure is for example applicable to the jointly owned commercial Abbott Point of Care (i-STAT™) electrochemical immunoassay system which performs sandwich immunoassays for several cardiac markers, including TnI, CKMB and BNP. Immunosensors and ways of operating them in single-use test devices are described in jointly owned Publication Nos. US 20030170881, US 20040018577, US 20050054078, and US 20060160164, each of which is incorporated herein by reference. Additional background on the manufacture of electrochemical and other types of immunosensors is found in jointly owned U.S. Pat. No. 5,063,081 which is also incorporated by reference.

By way of example, not of limitation, examples of the present invention shall now be given.

Example 1

Detection Antibody Conjugates

General Conjugation Procedure: Detection antibody was dissolved in a conjugation buffer (100 mM sodium phosphate, 150 mM NaCl, pH 8.0) to give a concentration of 1-10 mg/mL (6.25-62.5 µM). Acridinium, 9-[[[4-[(2,5-dioxo-1-pyrrolidinyl)oxy]-4-oxobutyl][(4-methylphenyl)sulfonyl]amino]carbonyl]-10-(3-sulfopropyl)-, inner salt, 2 (Adamczyk, M.; Chen, Y.-Y.; Mattingly, P. G.; Pan, Y. *J. Org. Chem.* 1998, 63, 5636-5639) labeling reagent was prepared in N,N-dimethylformamide (DMF) at a concentration of 1-50 mM, as shown in formula 2 below:

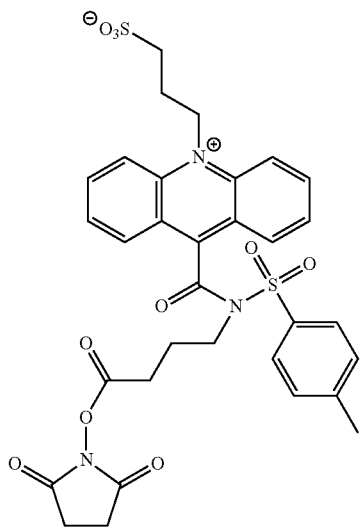

2

The selected antibody was treated with the acridinium-labeling reagent in a molar excess of 1-35 fold for 3-14 h at ambient temperature in the dark. Afterwards, the acridinium-9-carboxamide-antibody conjugate solution was dialyzed at ambient temperature over 20 hours using a 10 kilodalton molecular weight cutoff membrane against three volumes (1000× conjugate solution volume) of a dialysis buffer consisting of 10 mM phosphate buffered saline (PBS) containing 0.1% CHAPS (3-[(3-cholamidopropyl)dimethylammonio]-1-propanesulfonate).

The acridinium-9-carboxamide-antibody conjugate was analyzed by UV absorbance at 280/369 nm to determine the incorporation ratio (IR) of the acridinium-9-carboxamide label to the protein calculated according to the formula:

$$IR = A369/\epsilon369/([A280-(A369/4.1)]/\epsilon280)$$

where:

A280 and A369 are absorbance values obtained from the UV-visible spectrum of the conjugate;

4.1 is the ~A369/A280 ratio for an acridinium-9-carboxamide label;

$\epsilon280$ is the extinction coefficient for an antibody at 280 nm (i.e., for IgG mAb $\epsilon280$=210,000 $M^{-1}$ $cm^{-1}$); and $\epsilon369$ is the extinction coefficient for an acridinium-9-carboxamide label at 369 nm.

The average incorporation ratio for pooled fractions can range from 0.4-0.8× the molar excess of the acridinium-9-carboxamide labeling reagent used.

a) Murine anti-cardiac troponin-T 7G7 (Biodesign International/Meridian Life Sciences, Saco, Me.; cat no H86429M) mapped to epitope $cTnT_{60-70}$ was dialyzed against PBS to give a solution concentration of 0.35 mg/mL. After conjugation the calculated IR was 3.1.

b) Murine anti-cardiac troponin-T 7F4 (Fitzgerald Ind Intnl, Concord, Mass., cat no. 10R-T127C) mapped to epitope $cTnT_{61-70}$ was dialyzed against PBS to give a solution concentration of 0.469 mg/mL. After conjugation the calculated IR was 2.8.

c) Murine anti-cardiac troponin-T 1C11 (Fitzgerald Ind Intnl, Concord, Mass., cat no. 10R-T127D) mapped to epitope cTnT $cTnT_{95-181}$ was dialyzed against PBS to give a solution concentration of 0.469 mg/mL. After conjugation the calculated IR was 2.8.

d) Murine anti-cardiac troponin-T M8020207 (Fitzgerald Ind Intnl, Concord, Mass., cat no. 10R-T85D) mapped primarily to epitope cTnT $cTnT_{73-87}$ was dialyzed against PBS to give a solution concentration of 0.413 mg/mL. After conjugation the calculated IR was 4.1.

Example 2

Capture Antibodies on Magnetic Microparticles

Carboxy paramagnetic microparticles (5% solids, nominally 5 micron diameter, Polymer Labs, Varian, Inc. Amherst, Mass.) were diluted to a concentration of 1% solids in 2-(N-morpholino)ethanesulfonic acid buffer (MES, 2 mL, pH 6.2, 50 mM) then washed with MES buffer (3×, 2 mL), and finally, resuspended in MES (2 mL). The particles were activated by mixing with 1-ethyl-3-[3-dimethylaminopropyl]carbodiimide hydrochloride (20 µL of 11 mg/1.129 mL in water) for 20 min, then washed (MES, 2 mL) and re-suspended in MES (2 mL). Murine anti-cardiac troponin-T 1C11 (Fitzgerald Ind Intnl, Concord, Mass., cat no. 10R-T127D) was added to the suspension at 60 µg/mL. After mixing for 60 min the antigen coated particles were magnetically sequestered, and the antigen solution was replaced with a blocking solution consisting of 1% BSA in PBS (2 mL). After mixing for 30 min, the particles were washed with 1% BSA in PBS (3×, 2 mL) and finally, resuspended in 1% BSA in PBS (2 mL) and adjusted to a final concentration of 1% solids.

Microparticles were similarly prepared with the following murine anti-cardiac troponin-T antibodies: 7G7 (Biodesign International/Meridian Life Sciences, Saco, Me.; cat no H86429M); 7F4 (Fitzgerald Ind Intnl, Concord, Mass., cat no. 10R-T127C); and M8020207 (Fitzgerald Ind Intnl, Concord, Mass., cat no. 10R-T85D).

Example 3

Chemiluminescent Immunoassay Dose-Response for Combinations of Capture and Detection Antibodies A working suspension of each capture antibody microparticles prepared in Example 2 was prepared by dilution of the stock suspension to 0.05% solids in MES buffer (20 mM, pH 6.6) containing sucrose (13.6%) and antimicrobial agents. A working solution of each detection antibody conjugate was prepared by dilution of the stock solution to 10 ng/mL. Cardiac troponin-T (Biospacific, cat no. J34510359) standard solutions were prepared at 0, 0.25, 0.5, 1.0 and 2.0 μg/mL.

Figure 3:
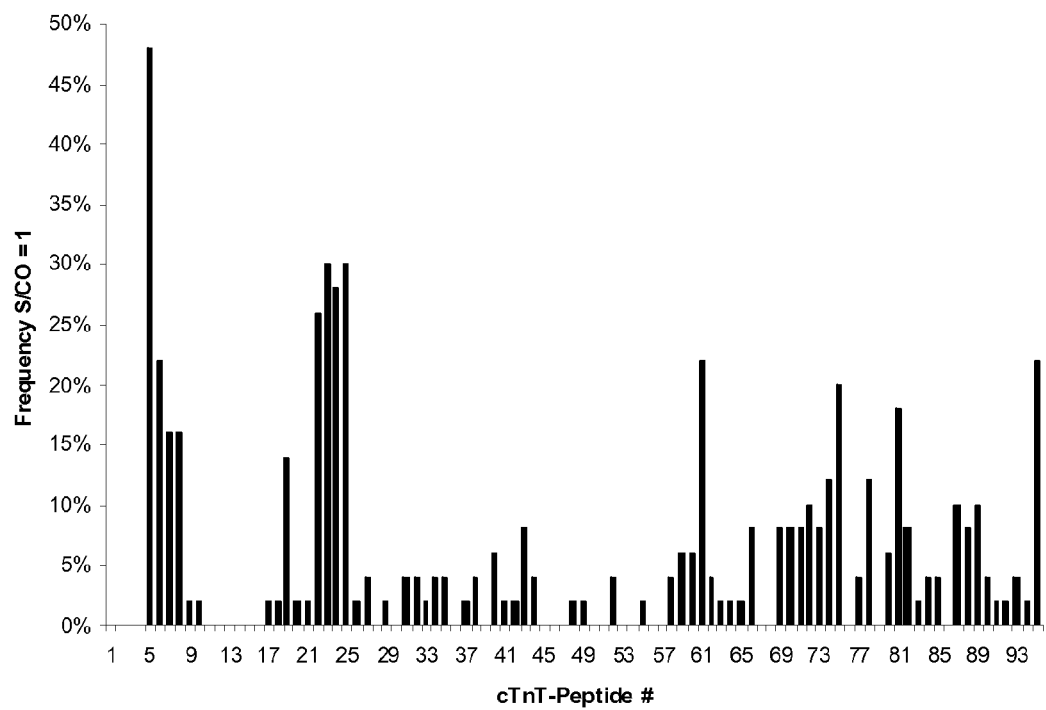
FIG. 3 is a frequency plot of cTnT autoantibody epitopes.

The assays were carried out on an ARCHITECT® i2000 instrument (Abbott Laboratories, Abbott Park, Ill.). Briefly, the cardiac troponin-T standard solution (10 μL) was diluted with ARCHITECT® PreIncubation Diluent (50 μL) and the capture antibody microparticles (50 μL) and incubated in the instrument reaction vessel. Following incubation, the microparticles were magnetically sequestered and washed with ARCHITECT® wash buffer. The detection antibody solution (50 μL) was added, the suspension incubated, and then the microparticles were washed again. ARCHITECT® pre-trigger solution containing hydrogen peroxide and ARCHITECT® trigger solution containing sodium hydroxide were then sequentially added and the chemiluminescent signal (relative light units, RLU) were recorded. The dose-response curves for combinations of capture and detection antibodies are shown in Table 1 and graphically in FIG. 1.

for 2 h. Afterwards the plates were washed with ARCHITECT® wash buffer and the response against each peptide was determined using chemiluminescent detection on a Berthold Mithras microplate reader (Berthold Technologies Inc, Oak Ridge, Tenn.). A mouse anti-human IgG acridinium labeled conjugate solution (100 μL) was added to each test well. After the conjugate was added to all test samples, the microplate was then sealed, placed on an orbital shaker at 28 rpm and incubated at 37° C. for 1 h. The conjugate solution was then removed and the wells of the microplate were washed with the ARCHITECT® Line Diluent (3×300 μL). The microplate was loaded into the instrument that had been equilibrated at 37° C. ARCHITECT® Pre-Trigger solution (100 μL) was dispensed to each well. After the pre-trigger solution was added, the plate was shaken for 72 s. Then the ARCHITECT® Trigger solution (100 μL) was dispensed to each well and chemiluminescent signal recorded for 2 s. FIG. 3 shows the frequency of reactive cardiac troponin-T epitopes found in human cardiac troponin-T autoantibodies.

TABLE 2 cTnT Antigen Peptide Library

| Peptide No. (SEQ ID NO.): | cTnT sequence | Sequence No. |
|---|---|---|
| 1 | SDIEEVVEEYEEEEQ | 1-15 |
| 2 | EEVVEEYEEEEQEEA | 4-18 |
| 3 | VEEYEEEEQEEAAVE | 7-21 |

TABLE 1

| | Detection conjugate/capture antibody (RLU) | | | | | | | | |
|---|---|---|---|---|---|---|---|---|---|
| Troponin-T (μg/mL) | 7G7/ 7F4 | 7G7/ M8020207 | 7G7/ 1C11 | 7F4/ 7G7 | 7F4/ M8020207 | 7F4/ 1C11 | M8020207/ 7G7 | M8020207/ 7F4 | M8020207/ 1C11 |
| 2 | 46829 | 305420 | 310518 | 6870 | 184343 | 185886 | 137713 | 100426 | 202062 |
| 1 | 29877 | 250755 | 238464 | 1469 | 136026 | 127325 | 106525 | 71224 | 157435 |
| 0.5 | 17246 | 163605 | 148894 | 618 | 82486 | 63012 | 70107 | 45245 | 105484 |
| 0.25 | 9081 | 96153 | 79374 | 452 | 38363 | 26439 | 42508 | 25611 | 66447 |
| 0 | 333 | 338 | 317 | 269 | 297 | 256 | 367 | 379 | 368 |

Example 4

Epitope Mapping of Autoantibodies to Cardiac Troponin T

Antibodies were screened against a biotinylated peptide library (Table 2) covering the entire human cTnT amino acid sequence as shown in FIG. 2 (UniProtKB/Swiss-Prot P45379 (TNNT2_HUMAN), initiator methionine removed, 297 aa, SEQ ID NO: 96), each peptide length, 15 aa; overlap, 12 aa; PEPscreen®, Sigma-Genosys, The Woodlands, Tex.) on streptavidin-coated microplates (Reacti-Bind™, Streptavidin; Pierce, Rockford, Ill.).

Thus, the peptides (100 μL, 1200 pmol/mL) were arrayed on the microplate; the microplate was then sealed and incubated/mixed for 1 h at ambient temperature. The microplate was then washed with ARCHITECT® wash buffer and aspirated to dryness. Samples (500 μL) were diluted with 9.5 mL of Axsym Troponin Preincubation diluent then arrayed (100 μL/well) to the microplates with the peptide library. The plates were sealed and incubated at 37° C., mixing at 28 rpm TABLE 2-continued cTnT Antigen Peptide Library

| Peptide No. (SEQ ID NO.): | cTnT sequence | Sequence No. |
|---|---|---|
| 4 | YEEEEQEEAAVEEEE | 10-24 |
| 5 | EEQEEAAVEEEEDWR | 13-27 |
| 6 | EEAAVEEEEDWREDE | 16-30 |
| 7 | AVEEEEDWREDEDEQ | 19-33 |
| 8 | EEEDWREDEDEQEEA | 22-36 |
| 9 | DWREDEDEQEEAAEE | 25-39 |
| 10 | EDEDEQEEAAEEDAE | 28-42 |
| 11 | DEQEEAAEEDAEAEA | 31-45 |
| 12 | EEAAEEDAEAEAETE | 34-48 |

TABLE 2-continued cTnT Antigen Peptide Library

| Peptide No. (SEQ ID NO.): | cTnT sequence | Sequence No. |
|---|---|---|
| 13 | AEEDAEAEAETEETR | 37-51 |
| 14 | DAEAEAETEETRAEE | 40-54 |
| 15 | AEAETEETRAEEDEE | 43-57 |
| 16 | ETEETRAEEDEEEEE | 46-60 |
| 17 | ETRAEEDEEEEAKE | 49-63 |
| 18 | AEEDEEEEAKEAED | 52-66 |
| 19 | DEEEEAKEAEDGPM | 55-69 |
| 20 | EEEAKEAEDGPMEES | 58-72 |
| 21 | AKEAEDGPMEESKPK | 61-75 |
| 22 | AEDGPMEESKPKPRS | 64-78 |
| 23 | GPMEESKPKPRSFMP | 67-81 |
| 24 | EESKPKPRSFMPNLV | 70-84 |
| 25 | KPKPRSFMPNLVPPK | 73-87 |
| 26 | PRSFMPNLVPPKIPD | 76-90 |
| 27 | FMPNLVPPKIPDGER | 79-93 |
| 28 | NLVPPKIPDGERVDF | 82-96 |
| 29 | PPKIPDGERVDFDDI | 85-99 |
| 30 | IPDGERVDFDDIHRK | 88-102 |
| 31 | GERVDFDDIHRKRME | 91-105 |
| 32 | VDFDDIHRKRMEKDL | 94-108 |
| 33 | DDIHRKRMEKDLNEL | 97-111 |
| 34 | HRKRMEKDLNELQAL | 100-114 |
| 35 | RMEKDLNELQALIEA | 103-117 |
| 36 | KDLNELQALIEAHFE | 106-120 |
| 37 | NELQALIEAHFENRK | 109-123 |
| 38 | QALIEAHFENRKKEE | 112-126 |
| 39 | IEAHFENRKKEEEEL | 115-129 |
| 40 | HFENRKKEEEELVSL | 118-132 |
| 41 | NRKKEEEELVSLKDR | 121-135 |
| 42 | KEEEELVSLKDRIER | 124-138 |
| 43 | EELVSLKDRIERRA | 127-141 |
| 44 | VSLKDRIERRAERA | 130-144 |
| 45 | KDRIERRRAERAEQQ | 133-147 |
| 46 | IERRRAERAEQQRIR | 136-150 |
| 47 | RRAERAEQQRIRNER | 139-153 |
| 48 | ERAEQQRIRNEREKE | 142-156 |
| 49 | EQQRIRNEREKERQN | 145-159 |
| 50 | RIRNEREKERQNRLA | 148-162 |
| 51 | NEREKERQNRLAEER | 151-165 |
| 52 | EKERQNRLAEERARR | 154-168 |
| 53 | RQNRLAEERARREEE | 157-171 |
| 54 | RLAEERARREEEENR | 160-174 |
| 55 | EERARREEEENRRKA | 163-177 |
| 56 | ARREEEENRRKAEDE | 166-180 |
| 57 | EEEENRRKAEDEARK | 169-183 |
| 58 | ENRRKAEDEARKKKA | 172-186 |
| 59 | RKAEDEARKKKALSN | 175-189 |
| 60 | EDEARKKKALSNMMH | 178-192 |
| 61 | ARKKKALSNMMHFGG | 181-195 |
| 62 | KKALSNMMHFGGYIQ | 184-198 |
| 63 | LSNMMHFGGYIQKQA | 187-201 |
| 64 | MMHFGGYIQKQAQTE | 190-204 |
| 65 | FGGYIQKQAQTERKS | 193-207 |
| 66 | YIQKQAQTERKSGKR | 196-210 |
| 67 | KQAQTERKSGKRQTE | 199-213 |
| 68 | QTERKSGKRQTEREK | 202-216 |
| 69 | RKSGKRQTEREKKKK | 205-219 |
| 70 | GKRQTEREKKKKILA | 208-222 |
| 71 | QTEREKKKKILAERR | 211-225 |
| 72 | REKKKKILAERRKVL | 214-228 |
| 73 | KKKILAERRKVLAID | 217-231 |
| 74 | ILAERRKVLAIDHLN | 220-234 |
| 75 | ERRKVLAIDHLNEDQ | 223-237 |
| 76 | KVLAIDHLNEDQLRE | 226-240 |
| 77 | AIDHLNEDQLREKAK | 229-243 |
| 78 | HLNEDQLREKAKELW | 232-246 |
| 79 | EDQLREKAKELWQSI | 235-249 |
| 80 | LREKAKELWQSIYNL | 238-252 |
| 81 | KAKELWQSIYNLEAE | 241-255 |
| 82 | ELWQSIYNLEAEKFD | 244-258 |
| 83 | QSIYNLEAEKFDLQE | 247-261 |
| 84 | YNLEAEKFDLQEKFK | 250-264 |
| 85 | EAEKFDLQEKFKQQK | 253-267 |
| 86 | KFDLQEKFKQQKYEI | 256-270 |

TABLE 2-continued cTnT Antigen Peptide Library

| Peptide No. (SEQ ID NO.): | cTnT sequence | Sequence No. |
|---|---|---|
| 87 | LQEKFKQQKYEINVL | 259-273 |
| 88 | KFKQQKYEINVLRNR | 262-276 |
| 89 | QQKYEINVLRNRIND | 265-279 |
| 90 | YEINVLRNRINDNQK | 268-282 |
| 91 | NVLRNRINDNQKVSK | 271-285 |
| 92 | RNRINDNQKVSKTRG | 274-288 |
| 93 | INDNQKVSKTRGKAK | 277-291 |
| 94 | NQKVSKTRGKAKVTG | 280-294 |
| 95 | VSKTRGKAKVTGRWK | 283-297 |

Example 5

Epitope Mapping of Monoclonal Antibodies to Cardiac Troponin-T

Murine anti-cardiac troponin-T M8020207 acridinium-9-carboxyamide conjugate from Example 1 was screened against a biotinylated peptide library (Table 2, Example 4). The conjugate was diluted to 100 ng/mL then the conjugate solution (100 µL) was added to each test well. After the conjugate was added, the microplate was then sealed, placed on an orbital shaker at 28 rpm and incubated at 37° C. for 1 h. The conjugate solution was then removed and the wells of the microplate were washed with the ARCHITECT® Line Diluent (3×300 µL). The microplate was loaded into the instrument that had been equilibrated at 37° C. ARCHITECT® Pre-Trigger solution (100 µL) was dispensed to each well. After the pre-trigger solution was added, the plate was shaken for 72 s. Then the ARCHITECT® Trigger solution (100 µL) was dispensed to each well and chemiluminescent signal recorded for 2 s.

Figure 4:
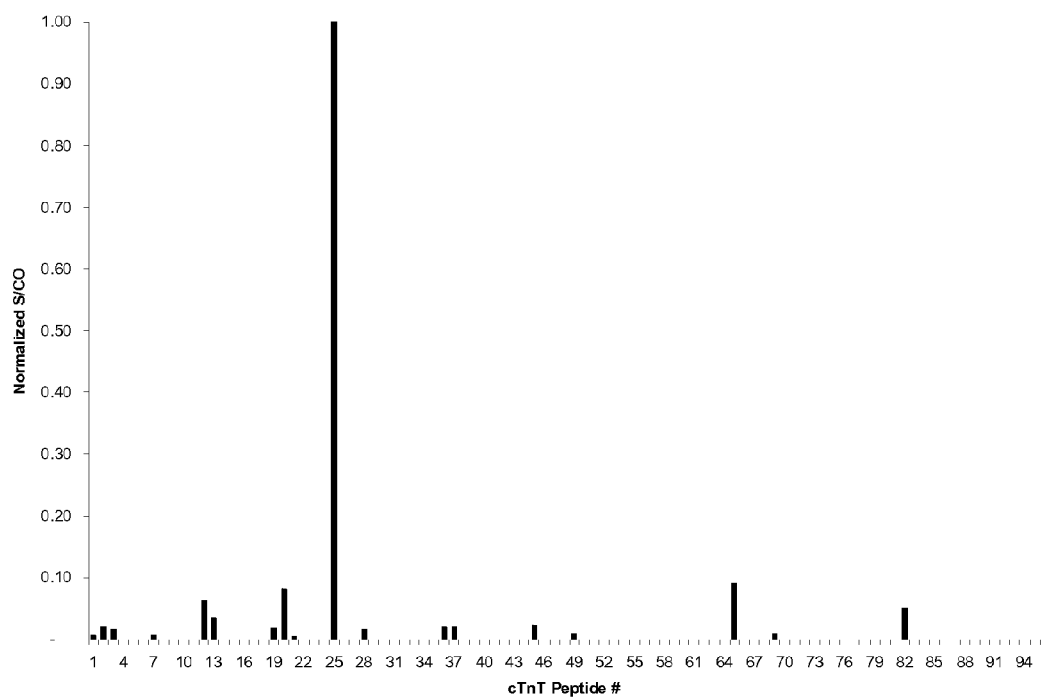
FIG. 4 is an epitope map of murine anti-cardiac troponin-T M8020207.

As shown in FIG. 4, the primary response was to peptide 25 corresponding to $cTnT_{73-87}$.

Figure 5:
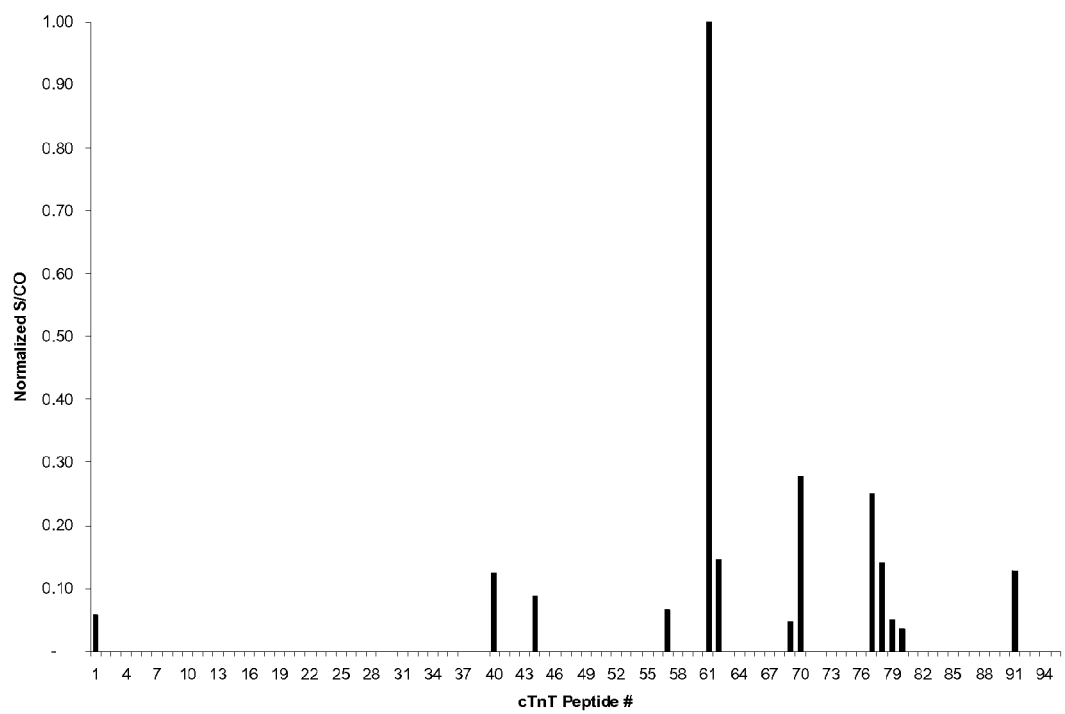
FIG. 5 is an epitope map of murine anti-cardiac troponin-T 1C11.

Murine anti-cardiac troponin-T 1C11 from Example 1 was screened against a biotinylated peptide library (Table 2, Example 4). The antibody was diluted to 100 ng/mL, then 100 µL was added to each test well. The plate was sealed and incubated at 37° C., mixing at 28 rpm for 2 h. Afterwards the plates were washed with ARCHITECT® wash buffer. A goat anti-mouse IgG acridinium labeled conjugate solution (100 µL) was added to each test well. After the conjugate was added to all test samples, the microplate was then sealed, placed on an orbital shaker at 28 rpm and incubated at 37° C. for 1 h. The conjugate solution was then removed and the wells of the microplate were washed with the ARCHITECT® Line Diluent (3×300 µL). The microplate was loaded into the instrument that had been equilibrated at 37° C. ARCHITECT® Pre-Trigger solution (100 µL) was dispensed to each well. After the pre-trigger solution was added, the plate was shaken for 72 s. Then the ARCHITECT® Trigger solution (100 µL) was dispensed to each well and chemiluminescent signal recorded for 2 s. As shown in FIG. 5, the primary epitopic response was to peptide 61 corresponding to $cTnT_{181-195}$.

Example 6

Standard Curve for Cardiac Troponin-T

Murine anti-cardiac troponin-T M8020207 coated microparticles from Example 2 were diluted to 0.3% solids. Murine anti-cardiac troponin-T 7G7 acridinium-9-carboxyamide conjugate from Example 1 was diluted to 30 ng/mL. Standard solutions were made from human cardiac troponin I-T-C complex (HyTest, Turku Finland, catalog no. 8T62) to give cTnT concentrations: 0, 7.0, 14.0, 42.0, and 279.0 pM. Three test samples were prepared by spiking hcTnITC into negative human plasma to give nominal cTnT concentrations of 0, 7.0 and 42 pM. The standard solutions and human plasma samples were analyzed on an ARCHITECT® i2000 as in Example 3. A point to point calibration curve was plotted (RLU vs cTnT concentration). The results are listed in Table 3.

TABLE 3

Magnetic microparticle cardiac troponin T assay results

| Sample | RLU | pM cTnT |
|---|---|---|
| Cal A | 2,369 | 0 |
| Cal B | 15,275 | 7 |
| Cal C | 28,071 | 14 |
| Cal D | 81,462 | 42 |
| Cal E | 422,814 | 279 |
| Negative plasma | 2,074 | #N/A |
| Spiked plasma @7 pM | 13,788 | 6.18 |
| Spiked plasma @42 pM | 74,126 | 38.07 |

One skilled in the art would readily appreciate that the immunoassays described in the present disclosure are well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

The present disclosure illustratively described herein suitably may be practiced in the absence of any element or elements, limitation or limitations which are not specifically disclosed herein. Thus, for example, in each instance herein any of the terms "comprising," "consisting essentially of" and "consisting" of may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An immunoassay for quantifying an amount of cardiac troponin-T (cTnT) in a test sample, the immunoassay comprising the steps of:
   a) contacting a test sample suspected of containing cTnT with n capture antibodies (C) that bind to at least n epitopes on cTnT to form a mixture comprising n-capture antibody:cTnT complex $(C_1)(C_2)...(Cn)(cTnT)$, wherein n is an integer from 1 to 10; and
   b) contacting said mixture comprising a n-capture antibody-cTnT epitope complex $(C_1)(C_2)...(Cn)(cTnT)$ with n' detection antibodies (D) that bind to n' epitopes on the cTnT to form a n'-detection antibody:n-capture antibody:cTnT measurable assembly $(D_1)(D_2)...(Dn')$ $(C_1)(C_2)...(Cn)(cTnT)$; and
   wherein n' and n are independently an integer from 1 to 10, and antibodies C and D bind to (n +n') different epitopes of cTnT,
   wherein the sum of n and n' is greater than 2, and
   wherein each antibody D binds to at least one epitope on cTnT that is different than any of the epitopes to which any of the antibodies C bind.

2. The immunoassay of claim 1, wherein an optical, electrical, or change-of-state signal of the measurable assembly is measured.

3. The immunoassay of claim 1 or 2, wherein the detection antibodies are conjugated to a detectable label, wherein the detectable label is an enzyme, oligonucleotide, nanoparticle chemiluminophore, fluorophore, fluorescence quencher, chemiluminescence quencher, or biotin.

4. The immunoassay of claim 1 or 2, wherein the capture antibodies, the detection antibodies or capture and detection antibodies comprise humanized antibodies.

5. The immunoassay of claim 1 or 2, wherein the detection antibodies comprise humanized antibodies complexed with an anti-human IgG antibody.

6. The immunoassay of claim 5, wherein said anti-human IgG antibody is conjugated to a detectable label, wherein the detectable label is an enzyme, oligonucleotide, nanoparticle chemiluminophore, fluorophore, fluorescence quencher, chemiluminescence quencher, or biotin.

7. The immunoassay of claim 2, wherein the optical signal is measured as a cTnT concentration dependent change in chemiluminescence, fluorescence, phosphorescence, electrochemiluminescence, ultraviolet absorption, visible absorption, infrared absorption, refraction, surface plasmon resonance.

8. The immunoassay of claim 2, wherein the electrical signal is measured as a troponin-T concentration dependent change in current, resistance, potential, mass to charge ratio, or ion count.

9. The immunoassay of claim 2, wherein the change-of-state signal is measured as a troponin-T concentration dependent change in size, solubility, mass, or resonance.

10. The immunoassay of claim 1 or 2, wherein the capture antibodies are immobilized on a solid phase.

11. The immunoassay of claim 10, wherein the solid phase is selected from the group consisting of a magnetic particle, bead, test tube, microtiter plate, cuvette, membrane, a scaffolding molecule, quartz crystal, film, filter paper, disc and chip.

* * * * *

UNITED STATES PATENT AND TRADEMARK OFFICE
CERTIFICATE OF CORRECTION

PATENT NO.        : 8,835,120 B2                                                Page 1 of 1
APPLICATION NO.   : 12/629736
DATED             : September 16, 2014
INVENTOR(S)       : Maciej Adamczyk, Jeffrey R. Brashear and Phillip G. Mattingly It is certified that error appears in the above-identified patent and that said Letters Patent is hereby corrected as shown below:

In the Claims

Column 67, claim 1,
Line 22 "on the cTnT to form a" -- should read -- "on the cTnT <u>of step (a)</u> to form a"

Column 68, claim 7,
Line 24 "tion, infrared absorption, refraction, surface" should read -- "tion, infrared absorption, refraction, <u>or</u> surface"

Signed and Sealed this
Twenty-eighth Day of April, 2015

Michelle K. Lee
*Director of the United States Patent and Trademark Office*

SEQUENCE LISTING

<160> NUMBER OF SEQ ID NOS: 96

<210> SEQ ID NO 1
<211> LENGTH: 15
<212> TYPE: PRT
<213> ORGANISM: Homo sapiens

<400> SEQUENCE: 1

Ser Asp Ile Glu Glu Val Val Glu Glu Tyr Glu Glu Glu Glu Gln
1               5                   10                  15

<210> SEQ ID NO 2
<211> LENGTH: 15
<212> TYPE: PRT
<213> ORGANISM: Homo sapiens

<400> SEQUENCE: 2

Glu Glu Val Val Glu Glu Tyr Glu Glu Glu Gln Glu Glu Ala
1               5                   10                  15

<210> SEQ ID NO 3
<211> LENGTH: 15
<212> TYPE: PRT
<213> ORGANISM: Homo sapiens

<400> SEQUENCE: 3

Val Glu Glu Tyr Glu Glu Glu Gln Glu Glu Ala Ala Val Glu
1               5                   10                  15

<210> SEQ ID NO 4
<211> LENGTH: 15
<212> TYPE: PRT
<213> ORGANISM: Homo sapiens

<400> SEQUENCE: 4

Tyr Glu Glu Glu Glu Gln Glu Glu Ala Ala Val Glu Glu Glu Glu
1               5                   10                  15

<210> SEQ ID NO 5
<211> LENGTH: 15
<212> TYPE: PRT
<213> ORGANISM: Homo sapiens

<400> SEQUENCE: 5

Glu Glu Gln Glu Glu Ala Ala Val Glu Glu Glu Glu Asp Trp Arg
1               5                   10                  15

<210> SEQ ID NO 6
<211> LENGTH: 15
<212> TYPE: PRT
<213> ORGANISM: Homo sapiens

<400> SEQUENCE: 6

Glu Glu Ala Ala Val Glu Glu Glu Glu Asp Trp Arg Glu Asp Glu
1               5                   10                  15

<210> SEQ ID NO 7
<211> LENGTH: 15
<212> TYPE: PRT
<213> ORGANISM: Homo sapiens

<400> SEQUENCE: 7

Ala Val Glu Glu Glu Glu Asp Trp Arg Glu Asp Glu Asp Glu Gln
1               5                   10                  15

<210> SEQ ID NO 8
<211> LENGTH: 15
<212> TYPE: PRT
<213> ORGANISM: Homo sapiens

<400> SEQUENCE: 8

Glu Glu Glu Asp Trp Arg Glu Asp Glu Asp Gln Glu Glu Ala
1               5                   10                  15

<210> SEQ ID NO 9
<211> LENGTH: 15
<212> TYPE: PRT
<213> ORGANISM: Homo sapiens

<400> SEQUENCE: 9

Asp Trp Arg Glu Asp Glu Asp Gln Glu Glu Ala Ala Glu
1               5                   10                  15

<210> SEQ ID NO 10
<211> LENGTH: 15
<212> TYPE: PRT
<213> ORGANISM: Homo sapiens

<400> SEQUENCE: 10

Glu Asp Glu Asp Glu Gln Glu Ala Ala Glu Glu Asp Ala Glu
1               5                   10                  15

<210> SEQ ID NO 11
<211> LENGTH: 15
<212> TYPE: PRT
<213> ORGANISM: Homo sapiens

<400> SEQUENCE: 11

Asp Glu Gln Glu Glu Ala Ala Glu Glu Asp Ala Glu Ala Glu Ala
1               5                   10                  15

<210> SEQ ID NO 12
<211> LENGTH: 15
<212> TYPE: PRT
<213> ORGANISM: Homo sapiens

<400> SEQUENCE: 12

Glu Glu Ala Ala Glu Glu Asp Ala Glu Ala Glu Ala Glu Thr Glu
1               5                   10                  15

<210> SEQ ID NO 13
<211> LENGTH: 15
<212> TYPE: PRT
<213> ORGANISM: Homo sapiens

<400> SEQUENCE: 13

Ala Glu Glu Asp Ala Glu Ala Glu Ala Glu Thr Glu Glu Thr Arg
1               5                   10                  15

<210> SEQ ID NO 14
<211> LENGTH: 15
<212> TYPE: PRT
<213> ORGANISM: Homo sapiens

<400> SEQUENCE: 14

Asp Ala Glu Ala Glu Ala Glu Thr Glu Glu Thr Arg Ala Glu Glu
1               5                   10                  15

<210> SEQ ID NO 15

```
<211> LENGTH: 15
<212> TYPE: PRT
<213> ORGANISM: Homo sapiens

<400> SEQUENCE: 15

Ala Glu Ala Glu Thr Glu Glu Thr Arg Ala Glu Glu Asp Glu Glu
1               5                   10                  15

<210> SEQ ID NO 16
<211> LENGTH: 15
<212> TYPE: PRT
<213> ORGANISM: Homo sapiens

<400> SEQUENCE: 16

Glu Thr Glu Glu Thr Arg Ala Glu Glu Asp Glu Glu Glu Glu Glu
1               5                   10                  15

<210> SEQ ID NO 17
<211> LENGTH: 15
<212> TYPE: PRT
<213> ORGANISM: Homo sapiens

<400> SEQUENCE: 17

Glu Thr Arg Ala Glu Glu Asp Glu Glu Glu Glu Glu Ala Lys Glu
1               5                   10                  15

<210> SEQ ID NO 18
<211> LENGTH: 15
<212> TYPE: PRT
<213> ORGANISM: Homo sapiens

<400> SEQUENCE: 18

Ala Glu Glu Asp Glu Glu Glu Glu Ala Lys Glu Ala Glu Asp
1               5                   10                  15

<210> SEQ ID NO 19
<211> LENGTH: 15
<212> TYPE: PRT
<213> ORGANISM: Homo sapiens

<400> SEQUENCE: 19

Asp Glu Glu Glu Glu Glu Ala Lys Glu Ala Glu Asp Gly Pro Met
1               5                   10                  15

<210> SEQ ID NO 20
<211> LENGTH: 15
<212> TYPE: PRT
<213> ORGANISM: Homo sapiens

<400> SEQUENCE: 20

Glu Glu Glu Ala Lys Glu Ala Glu Asp Gly Pro Met Glu Glu Ser
1               5                   10                  15

<210> SEQ ID NO 21
<211> LENGTH: 15
<212> TYPE: PRT
<213> ORGANISM: Homo sapiens

<400> SEQUENCE: 21

Ala Lys Glu Ala Glu Asp Gly Pro Met Glu Glu Ser Lys Pro Lys
1               5                   10                  15

<210> SEQ ID NO 22
<211> LENGTH: 15
<212> TYPE: PRT
```

<213> ORGANISM: Homo sapiens

<400> SEQUENCE: 22

Ala Glu Asp Gly Pro Met Glu Glu Ser Lys Pro Lys Pro Arg Ser
1               5                   10                  15

<210> SEQ ID NO 23
<211> LENGTH: 15
<212> TYPE: PRT
<213> ORGANISM: Homo sapiens

<400> SEQUENCE: 23

Gly Pro Met Glu Glu Ser Lys Pro Lys Pro Arg Ser Phe Met Pro
1               5                   10                  15

<210> SEQ ID NO 24
<211> LENGTH: 15
<212> TYPE: PRT
<213> ORGANISM: Homo sapiens

<400> SEQUENCE: 24

Glu Glu Ser Lys Pro Lys Pro Arg Ser Phe Met Pro Asn Leu Val
1               5                   10                  15

<210> SEQ ID NO 25
<211> LENGTH: 15
<212> TYPE: PRT
<213> ORGANISM: Homo sapiens

<400> SEQUENCE: 25

Lys Pro Lys Pro Arg Ser Phe Met Pro Asn Leu Val Pro Pro Lys
1               5                   10                  15

<210> SEQ ID NO 26
<211> LENGTH: 15
<212> TYPE: PRT
<213> ORGANISM: Homo sapiens

<400> SEQUENCE: 26

Pro Arg Ser Phe Met Pro Asn Leu Val Pro Pro Lys Ile Pro Asp
1               5                   10                  15

<210> SEQ ID NO 27
<211> LENGTH: 15
<212> TYPE: PRT
<213> ORGANISM: Homo sapiens

<400> SEQUENCE: 27

Phe Met Pro Asn Leu Val Pro Pro Lys Ile Pro Asp Gly Glu Arg
1               5                   10                  15

<210> SEQ ID NO 28
<211> LENGTH: 15
<212> TYPE: PRT
<213> ORGANISM: Homo sapiens

<400> SEQUENCE: 28

Asn Leu Val Pro Pro Lys Ile Pro Asp Gly Glu Arg Val Asp Phe
1               5                   10                  15

<210> SEQ ID NO 29
<211> LENGTH: 15
<212> TYPE: PRT
<213> ORGANISM: Homo sapiens

```
<400> SEQUENCE: 29

Pro Pro Lys Ile Pro Asp Gly Glu Arg Val Asp Phe Asp Asp Ile
1               5                   10                  15

<210> SEQ ID NO 30
<211> LENGTH: 15
<212> TYPE: PRT
<213> ORGANISM: Homo sapiens

<400> SEQUENCE: 30

Ile Pro Asp Gly Glu Arg Val Asp Phe Asp Asp Ile His Arg Lys
1               5                   10                  15

<210> SEQ ID NO 31
<211> LENGTH: 15
<212> TYPE: PRT
<213> ORGANISM: Homo sapiens

<400> SEQUENCE: 31

Gly Glu Arg Val Asp Phe Asp Asp Ile His Arg Lys Arg Met Glu
1               5                   10                  15

<210> SEQ ID NO 32
<211> LENGTH: 15
<212> TYPE: PRT
<213> ORGANISM: Homo sapiens

<400> SEQUENCE: 32

Val Asp Phe Asp Asp Ile His Arg Lys Arg Met Glu Lys Asp Leu
1               5                   10                  15

<210> SEQ ID NO 33
<211> LENGTH: 15
<212> TYPE: PRT
<213> ORGANISM: Homo sapiens

<400> SEQUENCE: 33

Asp Asp Ile His Arg Lys Arg Met Glu Lys Asp Leu Asn Glu Leu
1               5                   10                  15

<210> SEQ ID NO 34
<211> LENGTH: 15
<212> TYPE: PRT
<213> ORGANISM: Homo sapiens

<400> SEQUENCE: 34

His Arg Lys Arg Met Glu Lys Asp Leu Asn Glu Leu Gln Ala Leu
1               5                   10                  15

<210> SEQ ID NO 35
<211> LENGTH: 15
<212> TYPE: PRT
<213> ORGANISM: Homo sapiens

<400> SEQUENCE: 35

Arg Met Glu Lys Asp Leu Asn Glu Leu Gln Ala Leu Ile Glu Ala
1               5                   10                  15

<210> SEQ ID NO 36
<211> LENGTH: 15
<212> TYPE: PRT
<213> ORGANISM: Homo sapiens

<400> SEQUENCE: 36
```

```
Lys Asp Leu Asn Glu Leu Gln Ala Leu Ile Glu Ala His Phe Glu
1               5                   10                  15
```

<210> SEQ ID NO 37
<211> LENGTH: 15
<212> TYPE: PRT
<213> ORGANISM: Homo sapiens

<400> SEQUENCE: 37

```
Asn Glu Leu Gln Ala Leu Ile Glu Ala His Phe Glu Asn Arg Lys
1               5                   10                  15
```

<210> SEQ ID NO 38
<211> LENGTH: 15
<212> TYPE: PRT
<213> ORGANISM: Homo sapiens

<400> SEQUENCE: 38

```
Gln Ala Leu Ile Glu Ala His Phe Glu Asn Arg Lys Lys Glu Glu
1               5                   10                  15
```

<210> SEQ ID NO 39
<211> LENGTH: 15
<212> TYPE: PRT
<213> ORGANISM: Homo sapiens

<400> SEQUENCE: 39

```
Ile Glu Ala His Phe Glu Asn Arg Lys Lys Glu Glu Glu Glu Leu
1               5                   10                  15
```

<210> SEQ ID NO 40
<211> LENGTH: 15
<212> TYPE: PRT
<213> ORGANISM: Homo sapiens

<400> SEQUENCE: 40

```
His Phe Glu Asn Arg Lys Lys Glu Glu Glu Glu Leu Val Ser Leu
1               5                   10                  15
```

<210> SEQ ID NO 41
<211> LENGTH: 15
<212> TYPE: PRT
<213> ORGANISM: Homo sapiens

<400> SEQUENCE: 41

```
Asn Arg Lys Lys Glu Glu Glu Glu Leu Val Ser Leu Lys Asp Arg
1               5                   10                  15
```

<210> SEQ ID NO 42
<211> LENGTH: 15
<212> TYPE: PRT
<213> ORGANISM: Homo sapiens

<400> SEQUENCE: 42

```
Lys Glu Glu Glu Glu Leu Val Ser Leu Lys Asp Arg Ile Glu Arg
1               5                   10                  15
```

<210> SEQ ID NO 43
<211> LENGTH: 15
<212> TYPE: PRT
<213> ORGANISM: Homo sapiens

<400> SEQUENCE: 43

```
Glu Glu Leu Val Ser Leu Lys Asp Arg Ile Glu Arg Arg Arg Ala
1               5                   10                  15
```

```
<210> SEQ ID NO 44
<211> LENGTH: 15
<212> TYPE: PRT
<213> ORGANISM: Homo sapiens

<400> SEQUENCE: 44

Val Ser Leu Lys Asp Arg Ile Glu Arg Arg Ala Glu Arg Ala
1               5                   10                  15

<210> SEQ ID NO 45
<211> LENGTH: 15
<212> TYPE: PRT
<213> ORGANISM: Homo sapiens

<400> SEQUENCE: 45

Lys Asp Arg Ile Glu Arg Arg Ala Glu Arg Ala Glu Gln Gln
1               5                   10                  15

<210> SEQ ID NO 46
<211> LENGTH: 15
<212> TYPE: PRT
<213> ORGANISM: Homo sapiens

<400> SEQUENCE: 46

Ile Glu Arg Arg Arg Ala Glu Arg Ala Glu Gln Gln Arg Ile Arg
1               5                   10                  15

<210> SEQ ID NO 47
<211> LENGTH: 15
<212> TYPE: PRT
<213> ORGANISM: Homo sapiens

<400> SEQUENCE: 47

Arg Arg Ala Glu Arg Ala Glu Gln Gln Arg Ile Arg Asn Glu Arg
1               5                   10                  15

<210> SEQ ID NO 48
<211> LENGTH: 15
<212> TYPE: PRT
<213> ORGANISM: Homo sapiens

<400> SEQUENCE: 48

Glu Arg Ala Glu Gln Gln Arg Ile Arg Asn Glu Arg Glu Lys Glu
1               5                   10                  15

<210> SEQ ID NO 49
<211> LENGTH: 15
<212> TYPE: PRT
<213> ORGANISM: Homo sapiens

<400> SEQUENCE: 49

Glu Gln Gln Arg Ile Arg Asn Glu Arg Glu Lys Glu Arg Gln Asn
1               5                   10                  15

<210> SEQ ID NO 50
<211> LENGTH: 15
<212> TYPE: PRT
<213> ORGANISM: Homo sapiens

<400> SEQUENCE: 50

Arg Ile Arg Asn Glu Arg Glu Lys Glu Arg Gln Asn Arg Leu Ala
1               5                   10                  15
```

<210> SEQ ID NO 51
<211> LENGTH: 15
<212> TYPE: PRT
<213> ORGANISM: Homo sapiens

<400> SEQUENCE: 51

Asn Glu Arg Glu Lys Glu Arg Gln Asn Arg Leu Ala Glu Glu Arg
1               5                   10                  15

<210> SEQ ID NO 52
<211> LENGTH: 15
<212> TYPE: PRT
<213> ORGANISM: Homo sapiens

<400> SEQUENCE: 52

Glu Lys Glu Arg Gln Asn Arg Leu Ala Glu Glu Arg Ala Arg Arg
1               5                   10                  15

<210> SEQ ID NO 53
<211> LENGTH: 15
<212> TYPE: PRT
<213> ORGANISM: Homo sapiens

<400> SEQUENCE: 53

Arg Gln Asn Arg Leu Ala Glu Glu Arg Ala Arg Arg Glu Glu Glu
1               5                   10                  15

<210> SEQ ID NO 54
<211> LENGTH: 15
<212> TYPE: PRT
<213> ORGANISM: Homo sapiens

<400> SEQUENCE: 54

Arg Leu Ala Glu Glu Arg Ala Arg Arg Glu Glu Glu Glu Asn Arg
1               5                   10                  15

<210> SEQ ID NO 55
<211> LENGTH: 15
<212> TYPE: PRT
<213> ORGANISM: Homo sapiens

<400> SEQUENCE: 55

Glu Glu Arg Ala Arg Arg Glu Glu Glu Glu Asn Arg Arg Lys Ala
1               5                   10                  15

<210> SEQ ID NO 56
<211> LENGTH: 15
<212> TYPE: PRT
<213> ORGANISM: Homo sapiens

<400> SEQUENCE: 56

Ala Arg Arg Glu Glu Glu Glu Asn Arg Arg Lys Ala Glu Asp Glu
1               5                   10                  15

<210> SEQ ID NO 57
<211> LENGTH: 15
<212> TYPE: PRT
<213> ORGANISM: Homo sapiens

<400> SEQUENCE: 57

Glu Glu Glu Glu Asn Arg Arg Lys Ala Glu Asp Glu Ala Arg Lys
1               5                   10                  15

<210> SEQ ID NO 58
<211> LENGTH: 15

```
<212> TYPE: PRT
<213> ORGANISM: Homo sapiens

<400> SEQUENCE: 58

Glu Asn Arg Arg Lys Ala Glu Asp Glu Ala Arg Lys Lys Lys Ala
1               5                   10                  15

<210> SEQ ID NO 59
<211> LENGTH: 15
<212> TYPE: PRT
<213> ORGANISM: Homo sapiens

<400> SEQUENCE: 59

Arg Lys Ala Glu Asp Glu Ala Arg Lys Lys Lys Ala Leu Ser Asn
1               5                   10                  15

<210> SEQ ID NO 60
<211> LENGTH: 15
<212> TYPE: PRT
<213> ORGANISM: Homo sapiens

<400> SEQUENCE: 60

Glu Asp Glu Ala Arg Lys Lys Lys Ala Leu Ser Asn Met Met His
1               5                   10                  15

<210> SEQ ID NO 61
<211> LENGTH: 15
<212> TYPE: PRT
<213> ORGANISM: Homo sapiens

<400> SEQUENCE: 61

Ala Arg Lys Lys Lys Ala Leu Ser Asn Met Met His Phe Gly Gly
1               5                   10                  15

<210> SEQ ID NO 62
<211> LENGTH: 15
<212> TYPE: PRT
<213> ORGANISM: Homo sapiens

<400> SEQUENCE: 62

Lys Lys Ala Leu Ser Asn Met Met His Phe Gly Gly Tyr Ile Gln
1               5                   10                  15

<210> SEQ ID NO 63
<211> LENGTH: 15
<212> TYPE: PRT
<213> ORGANISM: Homo sapiens

<400> SEQUENCE: 63

Leu Ser Asn Met Met His Phe Gly Gly Tyr Ile Gln Lys Gln Ala
1               5                   10                  15

<210> SEQ ID NO 64
<211> LENGTH: 15
<212> TYPE: PRT
<213> ORGANISM: Homo sapiens

<400> SEQUENCE: 64

Met Met His Phe Gly Gly Tyr Ile Gln Lys Gln Ala Gln Thr Glu
1               5                   10                  15

<210> SEQ ID NO 65
<211> LENGTH: 15
<212> TYPE: PRT
<213> ORGANISM: Homo sapiens
```

<400> SEQUENCE: 65

Phe Gly Gly Tyr Ile Gln Lys Gln Ala Gln Thr Glu Arg Lys Ser
1               5                   10                  15

<210> SEQ ID NO 66
<211> LENGTH: 15
<212> TYPE: PRT
<213> ORGANISM: Homo sapiens

<400> SEQUENCE: 66

Tyr Ile Gln Lys Gln Ala Gln Thr Glu Arg Lys Ser Gly Lys Arg
1               5                   10                  15

<210> SEQ ID NO 67
<211> LENGTH: 15
<212> TYPE: PRT
<213> ORGANISM: Homo sapiens

<400> SEQUENCE: 67

Lys Gln Ala Gln Thr Glu Arg Lys Ser Gly Lys Arg Gln Thr Glu
1               5                   10                  15

<210> SEQ ID NO 68
<211> LENGTH: 15
<212> TYPE: PRT
<213> ORGANISM: Homo sapiens

<400> SEQUENCE: 68

Gln Thr Glu Arg Lys Ser Gly Lys Arg Gln Thr Glu Arg Glu Lys
1               5                   10                  15

<210> SEQ ID NO 69
<211> LENGTH: 15
<212> TYPE: PRT
<213> ORGANISM: Homo sapiens

<400> SEQUENCE: 69

Arg Lys Ser Gly Lys Arg Gln Thr Glu Arg Glu Lys Lys Lys Lys
1               5                   10                  15

<210> SEQ ID NO 70
<211> LENGTH: 15
<212> TYPE: PRT
<213> ORGANISM: Homo sapiens

<400> SEQUENCE: 70

Gly Lys Arg Gln Thr Glu Arg Glu Lys Lys Lys Ile Leu Ala
1               5                   10                  15

<210> SEQ ID NO 71
<211> LENGTH: 15
<212> TYPE: PRT
<213> ORGANISM: Homo sapiens

<400> SEQUENCE: 71

Gln Thr Glu Arg Glu Lys Lys Lys Lys Ile Leu Ala Glu Arg Arg
1               5                   10                  15

<210> SEQ ID NO 72
<211> LENGTH: 15
<212> TYPE: PRT
<213> ORGANISM: Homo sapiens

<400> SEQUENCE: 72

```
Arg Glu Lys Lys Lys Ile Leu Ala Glu Arg Arg Lys Val Leu
1               5                   10                  15
```

<210> SEQ ID NO 73
<211> LENGTH: 15
<212> TYPE: PRT
<213> ORGANISM: Homo sapiens

<400> SEQUENCE: 73

```
Lys Lys Lys Ile Leu Ala Glu Arg Arg Lys Val Leu Ala Ile Asp
1               5                   10                  15
```

<210> SEQ ID NO 74
<211> LENGTH: 15
<212> TYPE: PRT
<213> ORGANISM: Homo sapiens

<400> SEQUENCE: 74

```
Ile Leu Ala Glu Arg Arg Lys Val Leu Ala Ile Asp His Leu Asn
1               5                   10                  15
```

<210> SEQ ID NO 75
<211> LENGTH: 15
<212> TYPE: PRT
<213> ORGANISM: Homo sapiens

<400> SEQUENCE: 75

```
Glu Arg Arg Lys Val Leu Ala Ile Asp His Leu Asn Glu Asp Gln
1               5                   10                  15
```

<210> SEQ ID NO 76
<211> LENGTH: 15
<212> TYPE: PRT
<213> ORGANISM: Homo sapiens

<400> SEQUENCE: 76

```
Lys Val Leu Ala Ile Asp His Leu Asn Glu Asp Gln Leu Arg Glu
1               5                   10                  15
```

<210> SEQ ID NO 77
<211> LENGTH: 15
<212> TYPE: PRT
<213> ORGANISM: Homo sapiens

<400> SEQUENCE: 77

```
Ala Ile Asp His Leu Asn Glu Asp Gln Leu Arg Glu Lys Ala Lys
1               5                   10                  15
```

<210> SEQ ID NO 78
<211> LENGTH: 15
<212> TYPE: PRT
<213> ORGANISM: Homo sapiens

<400> SEQUENCE: 78

```
His Leu Asn Glu Asp Gln Leu Arg Glu Lys Ala Lys Glu Leu Trp
1               5                   10                  15
```

<210> SEQ ID NO 79
<211> LENGTH: 15
<212> TYPE: PRT
<213> ORGANISM: Homo sapiens

<400> SEQUENCE: 79

```
Glu Asp Gln Leu Arg Glu Lys Ala Lys Glu Leu Trp Gln Ser Ile
1               5                   10                  15
```

```
                    1               5              10              15

<210> SEQ ID NO 80
<211> LENGTH: 15
<212> TYPE: PRT
<213> ORGANISM: Homo sapiens

<400> SEQUENCE: 80

Leu Arg Glu Lys Ala Lys Glu Leu Trp Gln Ser Ile Tyr Asn Leu
1               5                   10                  15

<210> SEQ ID NO 81
<211> LENGTH: 15
<212> TYPE: PRT
<213> ORGANISM: Homo sapiens

<400> SEQUENCE: 81

Lys Ala Lys Glu Leu Trp Gln Ser Ile Tyr Asn Leu Glu Ala Glu
1               5                   10                  15

<210> SEQ ID NO 82
<211> LENGTH: 15
<212> TYPE: PRT
<213> ORGANISM: Homo sapiens

<400> SEQUENCE: 82

Glu Leu Trp Gln Ser Ile Tyr Asn Leu Glu Ala Glu Lys Phe Asp
1               5                   10                  15

<210> SEQ ID NO 83
<211> LENGTH: 15
<212> TYPE: PRT
<213> ORGANISM: Homo sapiens

<400> SEQUENCE: 83

Gln Ser Ile Tyr Asn Leu Glu Ala Glu Lys Phe Asp Leu Gln Glu
1               5                   10                  15

<210> SEQ ID NO 84
<211> LENGTH: 15
<212> TYPE: PRT
<213> ORGANISM: Homo sapiens

<400> SEQUENCE: 84

Tyr Asn Leu Glu Ala Glu Lys Phe Asp Leu Gln Glu Lys Phe Lys
1               5                   10                  15

<210> SEQ ID NO 85
<211> LENGTH: 15
<212> TYPE: PRT
<213> ORGANISM: Homo sapiens

<400> SEQUENCE: 85

Glu Ala Glu Lys Phe Asp Leu Gln Glu Lys Phe Lys Gln Gln Lys
1               5                   10                  15

<210> SEQ ID NO 86
<211> LENGTH: 15
<212> TYPE: PRT
<213> ORGANISM: Homo sapiens

<400> SEQUENCE: 86

Lys Phe Asp Leu Gln Glu Lys Phe Lys Gln Gln Lys Tyr Glu Ile
1               5                   10                  15
```

<210> SEQ ID NO 87
<211> LENGTH: 15
<212> TYPE: PRT
<213> ORGANISM: Homo sapiens

<400> SEQUENCE: 87

Leu Gln Glu Lys Phe Lys Gln Gln Lys Tyr Glu Ile Asn Val Leu
1               5                   10                  15

<210> SEQ ID NO 88
<211> LENGTH: 15
<212> TYPE: PRT
<213> ORGANISM: Homo sapiens

<400> SEQUENCE: 88

Lys Phe Lys Gln Gln Lys Tyr Glu Ile Asn Val Leu Arg Asn Arg
1               5                   10                  15

<210> SEQ ID NO 89
<211> LENGTH: 15
<212> TYPE: PRT
<213> ORGANISM: Homo sapiens

<400> SEQUENCE: 89

Gln Gln Lys Tyr Glu Ile Asn Val Leu Arg Asn Arg Ile Asn Asp
1               5                   10                  15

<210> SEQ ID NO 90
<211> LENGTH: 15
<212> TYPE: PRT
<213> ORGANISM: Homo sapiens

<400> SEQUENCE: 90

Tyr Glu Ile Asn Val Leu Arg Asn Arg Ile Asn Asp Asn Gln Lys
1               5                   10                  15

<210> SEQ ID NO 91
<211> LENGTH: 15
<212> TYPE: PRT
<213> ORGANISM: Homo sapiens

<400> SEQUENCE: 91

Asn Val Leu Arg Asn Arg Ile Asn Asp Asn Gln Lys Val Ser Lys
1               5                   10                  15

<210> SEQ ID NO 92
<211> LENGTH: 15
<212> TYPE: PRT
<213> ORGANISM: Homo sapiens

<400> SEQUENCE: 92

Arg Asn Arg Ile Asn Asp Asn Gln Lys Val Ser Lys Thr Arg Gly
1               5                   10                  15

<210> SEQ ID NO 93
<211> LENGTH: 15
<212> TYPE: PRT
<213> ORGANISM: Homo sapiens

<400> SEQUENCE: 93

Ile Asn Asp Asn Gln Lys Val Ser Lys Thr Arg Gly Lys Ala Lys
1               5                   10                  15

<210> SEQ ID NO 94

<211> LENGTH: 15
<212> TYPE: PRT
<213> ORGANISM: Homo sapiens

<400> SEQUENCE: 94

Asn Gln Lys Val Ser Lys Thr Arg Gly Lys Ala Lys Val Thr Gly
1               5                   10                  15

<210> SEQ ID NO 95
<211> LENGTH: 15
<212> TYPE: PRT
<213> ORGANISM: Homo sapiens

<400> SEQUENCE: 95

Val Ser Lys Thr Arg Gly Lys Ala Lys Val Thr Gly Arg Trp Lys
1               5                   10                  15

<210> SEQ ID NO 96
<211> LENGTH: 297
<212> TYPE: PRT
<213> ORGANISM: Homo sapiens

<400> SEQUENCE: 96

Ser Asp Ile Glu Glu Val Val Glu Glu Tyr Glu Glu Glu Gln Glu
1               5                   10                  15

Glu Ala Ala Val Glu Glu Glu Asp Trp Arg Glu Asp Glu Asp Glu
                20                  25                  30

Gln Glu Glu Ala Ala Glu Glu Asp Ala Glu Ala Glu Ala Glu Thr Glu
            35                  40                  45

Glu Thr Arg Ala Glu Glu Asp Glu Glu Glu Glu Ala Lys Glu Ala
        50                  55                  60

Glu Asp Gly Pro Met Glu Glu Ser Lys Pro Lys Pro Arg Ser Phe Met
65                  70                  75                  80

Pro Asn Leu Val Pro Pro Lys Ile Pro Asp Gly Glu Arg Val Asp Phe
                85                  90                  95

Asp Asp Ile His Arg Lys Arg Met Glu Lys Asp Leu Asn Glu Leu Gln
            100                 105                 110

Ala Leu Ile Glu Ala His Phe Glu Asn Arg Lys Lys Glu Glu Glu Glu
        115                 120                 125

Leu Val Ser Leu Lys Asp Arg Ile Glu Arg Arg Ala Glu Arg Ala
    130                 135                 140

Glu Gln Gln Arg Ile Arg Asn Glu Arg Glu Lys Glu Arg Gln Asn Arg
145                 150                 155                 160

Leu Ala Glu Glu Arg Ala Arg Arg Glu Glu Glu Asn Arg Arg Lys
                165                 170                 175

Ala Glu Asp Glu Ala Arg Lys Lys Lys Ala Leu Ser Asn Met Met His
            180                 185                 190

Phe Gly Gly Tyr Ile Gln Lys Gln Ala Gln Thr Glu Arg Lys Ser Gly
        195                 200                 205

Lys Arg Gln Thr Glu Arg Glu Lys Lys Lys Ile Leu Ala Glu Arg
    210                 215                 220

Arg Lys Val Leu Ala Ile Asp His Leu Asn Glu Asp Gln Leu Arg Glu
225                 230                 235                 240

Lys Ala Lys Glu Leu Trp Gln Ser Ile Tyr Asn Leu Glu Ala Glu Lys
                245                 250                 255

Phe Asp Leu Gln Glu Lys Phe Lys Gln Gln Lys Tyr Glu Ile Asn Val
            260                 265                 270

-continued

```
Leu Arg Asn Arg Ile Asn Asp Asn Gln Lys Val Ser Lys Thr Arg Gly
            275                 280                 285

Lys Ala Lys Val Thr Gly Arg Trp Lys
            290                 295
```